US009836185B2

(12) United States Patent
O'Mahony et al.

(10) Patent No.: US 9,836,185 B2
(45) Date of Patent: Dec. 5, 2017

(54) EXTRACORPOREAL BLOOD TREATMENT DATA INTERFACE

(71) Applicant: GAMBRO LUNDIA AB, Lund (SE)

(72) Inventors: John O'Mahony, Maple Grove, MN (US); Jonas Schaefer, St. Paul, MN (US); Andrew Wenger, Osseo, MN (US)

(73) Assignee: Gambro Lundia AB, Lund (SE)

( * ) Notice: Subject to any disclaimer, the term of this patent is extended or adjusted under 35 U.S.C. 154(b) by 174 days.

(21) Appl. No.: 14/653,020

(22) PCT Filed: Dec. 17, 2013

(86) PCT No.: PCT/US2013/075667
§ 371 (c)(1),
(2) Date: Jun. 17, 2015

(87) PCT Pub. No.: WO2014/105517
PCT Pub. Date: Jul. 3, 2014

(65) Prior Publication Data
US 2015/0355790 A1    Dec. 10, 2015

Related U.S. Application Data

(60) Provisional application No. 61/747,833, filed on Dec. 31, 2012.

(51) Int. Cl.
*G06F 3/048* (2013.01)
*G06F 3/0482* (2013.01)
(Continued)

(52) U.S. Cl.
CPC ........... *G06F 3/0482* (2013.01); *A61M 1/367* (2013.01); *G06F 3/0484* (2013.01);
(Continued)

(58) Field of Classification Search
CPC .................................................. G06F 19/3406
(Continued)

(56) References Cited

U.S. PATENT DOCUMENTS 5,441,636 A    8/1995  Chevallet
5,609,770 A    3/1997  Zimmerman
(Continued)

FOREIGN PATENT DOCUMENTS

CN    1234685 A    11/1999
CN    1282039      1/2001
(Continued)

OTHER PUBLICATIONS

PCT International Preliminary Report on Patentability for PCT/US2013/075667 dated Jul. 9, 2015 (16 pages).
(Continued)

*Primary Examiner* — William Titcomb
(74) *Attorney, Agent, or Firm* — Mueting, Raasch & Gebhardt, P.A.

(57) ABSTRACT

Extracorporeal blood treatment systems and methods to display and select various historical data for extracorporeal blood treatments. Historical data related to extracorporeal blood treatments may be displayed on a two-dimensional graph and in a list view that may be switched there between. Further, historical data may include various datasets (e.g., fluid datasets, patient fluid removal datasets, anticoagulation datasets, etc.) and event information that may be displayed simultaneously.

25 Claims, 21 Drawing Sheets

(51) Int. Cl.
  *A61M 1/36* (2006.01)
  *G06F 3/0484* (2013.01)
  *G06F 19/00* (2011.01)

(52) U.S. Cl.
  CPC ...... *G06F 3/04842* (2013.01); *G06F 19/3406* (2013.01); *G06F 19/3487* (2013.01); *A61M 2205/18* (2013.01); *A61M 2205/502* (2013.01)

(58) Field of Classification Search
  USPC ........................................................ 715/771
  See application file for complete search history.

(56) References Cited

U.S. PATENT DOCUMENTS

| | | | |
|---|---|---|---|
| 5,679,245 | A | 10/1997 | Manica |
| 5,762,805 | A | 6/1998 | Truitt |
| 5,776,345 | A | 7/1998 | Truitt |
| 5,788,851 | A * | 8/1998 | Kenley ............... A61M 1/14 210/143 |
| 5,910,252 | A | 6/1999 | Truitt |
| 5,951,485 | A | 9/1999 | Cyrus |
| 6,532,590 | B1 | 3/2003 | Chimoto |
| 7,081,091 | B2 | 7/2006 | Merrett |
| 7,100,105 | B1 | 8/2006 | Nishimura |
| 7,264,730 | B2 * | 9/2007 | Connell ............... A61M 1/16 210/138 |
| 7,461,333 | B2 | 12/2008 | Nishimura |
| 7,618,531 | B2 | 11/2009 | Sugioka |
| 7,640,055 | B2 * | 12/2009 | Geva .................. A61B 5/00 600/300 |
| 7,647,237 | B2 | 1/2010 | Malave |
| 7,757,183 | B2 | 7/2010 | Rutledge |
| 7,778,851 | B2 * | 8/2010 | Schoenberg ......... G06F 19/322 600/300 |
| 7,805,320 | B2 | 9/2010 | Deitsch |
| 7,988,850 | B2 | 8/2011 | Roncadi |
| 8,074,163 | B2 | 12/2011 | Nishimura |
| 8,108,861 | B2 | 1/2012 | Ino |
| 8,127,218 | B2 | 2/2012 | Nishimura |
| 8,267,881 | B2 * | 9/2012 | O'Mahony ......... A61M 1/34 210/645 |
| 8,287,736 | B2 | 10/2012 | Roncadi |
| 8,475,398 | B2 * | 7/2013 | O'Mahony ......... A61M 1/34 210/645 |
| 8,485,998 | B2 * | 7/2013 | Moll ................... G06F 19/3406 604/5.01 |
| 8,603,021 | B2 * | 12/2013 | Levin .................. A61M 1/34 210/321.71 |
| 8,956,292 | B2 * | 2/2015 | Wekell ............... A61B 5/02055 600/301 |
| 9,408,958 | B2 * | 8/2016 | Wang .................. A61M 1/16 |
| 2003/0208465 | A1 * | 11/2003 | Yurko ................. G06F 19/322 |
| 2004/0073098 | A1 * | 4/2004 | Geva .................. A61B 5/00 600/300 |
| 2004/0087888 | A1 * | 5/2004 | DiGianfilippo ...... A61K 9/0019 604/19 |
| 2004/0172301 | A1 * | 9/2004 | Mihai .................. A61B 5/0002 705/2 |
| 2006/0047538 | A1 * | 3/2006 | Condurso ............ G06F 19/326 705/3 |
| 2006/0155589 | A1 * | 7/2006 | Lane .................... A61B 5/0002 705/4 |
| 2006/0289342 | A1 | 12/2006 | Sugioka |
| 2008/0176210 | A1 | 7/2008 | Moll |
| 2008/0307353 | A1 | 12/2008 | Molducci |
| 2009/0005703 | A1 | 1/2009 | Fasciano |
| 2009/0054743 | A1 * | 2/2009 | Stewart ............... G06T 11/206 600/301 |
| 2009/0147006 | A1 | 6/2009 | Buck |
| 2009/0156988 | A1 * | 6/2009 | Ferren ................. A61B 5/0031 604/65 |
| 2009/0287191 | A1 * | 11/2009 | Ferren ................. A61B 5/0031 604/891.1 |
| 2010/0036268 | A1 * | 2/2010 | Ferren ................. G06F 19/3406 600/504 |
| 2010/0036269 | A1 * | 2/2010 | Ferren ................. A61B 5/02007 600/504 |
| 2010/0131293 | A1 | 5/2010 | Linthicum |
| 2010/0317950 | A1 | 12/2010 | Galley |
| 2011/0144573 | A1 * | 6/2011 | Rofougaran ........ A61B 5/411 604/66 |
| 2011/0169834 | A1 | 7/2011 | Dalesch |
| 2012/0154264 | A1 * | 6/2012 | Wang .................. A61M 1/16 345/156 |
| 2013/0193041 | A1 * | 8/2013 | Rohde ................. G06F 19/3406 210/143 |
| 2013/0317837 | A1 * | 11/2013 | Ballantyne ......... A61M 1/1037 705/2 |
| 2014/0188516 | A1 * | 7/2014 | Kamen ............... G06F 19/3406 705/3 |

FOREIGN PATENT DOCUMENTS

| | | |
|---|---|---|
| CN | 1770852 A | 5/2006 |
| CN | 101341489 | 1/2009 |
| EP | 1364666 | 11/2003 |
| EP | 2292284 | 3/2011 |
| WO | WO 2004/074966 | 9/2004 |
| WO | WO 2008/071753 | 6/2008 |
| WO | WO 2009/049276 | 4/2009 |
| WO | WO 2009/071200 | 6/2009 |
| WO | WO 2010/006147 | 1/2010 |
| WO | WO 2010/033503 | 3/2010 |
| WO | WO 2010/053626 | 5/2010 |
| WO | WO 2012/092919 | 7/2012 |

OTHER PUBLICATIONS

International Search Report and Written Opinion for PCT/US2013/075667 dated Apr. 3, 2014 (19 pages).

* cited by examiner

EXTRACORPOREAL BLOOD TREATMENT DATA INTERFACE

CROSS-REFERENCE

This application is the U.S. National Stage Application of International Application No. PCT/US2013/075667, filed Dec. 17, 2013 and published in English on Jul. 3, 2014 as International Publication No. WO 2014/105517 A1, which claims the benefit under 35 U.S.C. 119(e) of U.S. Provisional Application Ser. No. 61/747,833, filed Dec. 31, 2012; all of which are incorporated herein by reference in their entirety.

BACKGROUND

The disclosure herein relates to extracorporeal blood treatment. More particularly, the disclosure relates to user interfaces for display of data recorded (e.g., historical data) during extracorporeal blood treatments.

Many different parameters and/or events are logged, or recorded, during extracorporeal blood treatments that may be useful to review during a treatment or after a treatment is complete. For example, a user may want to view one or more logged parameters and events to ensure that a treatment is progressing adequately. Further, a user may want to view one or more logged parameters and events to determine what may have caused alarms during a treatment. Still further, a user may desire to view one or more logged parameters and events to diagnose problems with an extracorporeal blood treatment system.

SUMMARY

The present disclosure describes systems and methods that provide graphical user interfaces for viewing historical data (e.g., data recorded, or logged, during extracorporeal blood treatments). Such graphical user interfaces may include a two-dimensional graph and a plurality of different settings and/or filters to assist a user in viewing the historical data. Graphs may display information that is continuous and happens over a period of time. Further, the graphical user interfaces may include a chronological list view of all, or a selected group, of events that have occurred during extracorporeal blood treatments. A list view of events (e.g., an event log) may display information which occurs at a single point in time (e.g., at each event). Navigation between the two-dimensional graph and the list view may maintain that same position in time, e.g., such that a user may flip between the views to analyze and/or review the historical data without losing track of a selected position in time.

One exemplary extracorporeal blood treatment system may include a display apparatus including a graphical user interface. The graphical user interface may be configured to depict a two-dimensional graph and a time interval selection region. The two-dimensional graph may define a time axis representing time and a value axis extending relative to the time axis and representing at least one value. Further, the two-dimensional graph may define a viewable time frame extending from a first end region to a second end region along the time axis. The exemplary system may further include an input interface configured to allow a user to select one or more of a plurality of datasets to be plotted on the two-dimensional graph and a computing apparatus operatively coupled to the display apparatus and the input interface. The computing apparatus may be configured to display on the graphical user interface a time interval selection region and allow a user to use the input interface to select a time interval of a plurality of different time intervals using the time interval selection region of the graphical user interface. The plurality of different time intervals may include at least one dynamic time interval. The at least one dynamic time interval may define a time interval that is determined as a function of an occurrence of at least one event (e.g., the at least one dynamic time interval may extend from an event of the at least one event to the present time, the at least one dynamic time interval may extend from a first event of the at least one event to a second event of the at least one event, etc.). The computing apparatus may be further configured to display one or more selected datasets plotted on the two-dimensional graph of the graphical user interface for the selected time interval in the viewable time frame.

One exemplary method for an extracorporeal blood treatment system may include providing a graphical user interface including a two-dimensional graph and a time interval selection region. The two-dimensional graph may define a time axis representing time and a value axis extending relative to the time axis and representing at least one value. Further, the two-dimensional graph may define a viewable time frame extending from a first end region to a second end region along the time axis. The exemplary method may further include providing an input interface configured to allow a user to select one or more of a plurality of datasets to be plotted on the two-dimensional graph and allowing a user to use the input interface to select a time interval of a plurality of different time intervals using the time interval selection region of the graphical user interface. The plurality of different time intervals may include at least one dynamic time interval. The at least one dynamic time interval may define a time interval that is determined as a function of an occurrence of at least one event (e.g., the at least one dynamic time interval may extend from an event of the at least one event to the present time, the at least one dynamic time interval may extend from a first event of the at least one event to a second event of the at least one event, etc.). The exemplary method may further include displaying one or more selected datasets plotted on the two-dimensional graph for the selected time interval in the viewable time frame.

One exemplary extracorporeal blood treatment system may include a display apparatus including a graphical user interface. The graphical user interface may be configured to depict a two-dimensional graph and an event type selection region. The two-dimensional graph may define a time axis representing time and a value axis extending relative to the time axis and representing at least one value. Further, the two-dimensional graph may define a viewable time frame extending from a first end region to a second end region along the time axis. The exemplary system may further include an input interface configured to allow a user to select one or more of a plurality of datasets to be plotted on the two-dimensional graph and a computing apparatus operatively coupled to the display apparatus and the input interface. The computing apparatus may be configured to display one or more selected datasets plotted on a two-dimensional graph of the graphical user interface in the viewable time frame, display on the graphical user interface an event type selection region, allow a user to use the input interface to select one or more event types of a plurality of different event types using the event type selection region of the graphical user interface, and display on the graphical user interface one or more graphical elements representing events of the one or more selected event types at locations proximate the two-dimensional graph (e.g., located below the time axis of the two-dimensional graph, etc.) when the events occurred in the viewable time frame.

One exemplary method for an extracorporeal blood treatment system may include providing a graphical user interface including a two-dimensional graph and an event type selection region. The two-dimensional graph may define a time axis representing time and a value axis extending relative to the time axis and representing at least one value. The two-dimensional graph may define a viewable time frame extending from a first end region to a second end region along the time axis. The exemplary method may further include providing an input interface configured to allow a user to select one or more of a plurality of datasets to be plotted on the two-dimensional graph, displaying one or more selected datasets plotted on the two-dimensional graph of the graphical user interface in the viewable time frame, allowing a user to use the input interface to select one or more event types of a plurality of different event types using the event type selection region of the graphical user interface, and displaying on the graphical user interface one or more graphical elements representing events of the one or more selected event types at locations proximate the two-dimensional graph (e.g., located below the time axis of the two-dimensional graph, etc.) when the events occurred in the viewable time frame.

One exemplary extracorporeal blood treatment system may include a display apparatus including a graphical user interface. The graphical user interface may be configured to depict a two-dimensional graph and a list view (e.g., only one of the two-dimensional graph and the list view may be displayed on the graphical user interface at the same time). The two-dimensional graph may define a time axis representing time and a value axis extending relative to the time axis and representing a value. Further, the two-dimensional graph may define a viewable time frame extending from a first end region to a second end region along the time axis. The list view may include a chronological list of events. The exemplary system may further include an input interface configured to allow a user to select one or more of a plurality of datasets to be plotted on the two-dimensional graph and a computing apparatus operatively coupled to the display apparatus and the input interface. The computing apparatus may be configured to display on a graphical user interface one or more selected datasets plotted on a two-dimensional graph in the viewable time frame, display on the graphical user interface one or more graphical elements representing events at locations proximate the two-dimensional graph when the events occurred in the viewable time frame, allow a user to use the input interface to switch to a list view from the two-dimensional graph, and display on the graphical user interface the list view including a chronological list of events corresponding to at least a portion of the viewable time frame of the two-dimensional graph.

One exemplary method for an extracorporeal blood treatment system may include providing a graphical user interface including a two-dimensional graph and a list view (e.g., only one of the two-dimensional graph and the list view may be displayed on the graphical user interface at the same time). The two-dimensional graph may define a time axis representing time and a value axis extending relative to the time axis and representing a value. Further, the two-dimensional graph may define a viewable time frame extending from a first end region to a second end region along the time axis. The list view may include a chronological list of events. The exemplary method may further include providing an input interface configured to allow a user to select one or more of a plurality of datasets to be plotted on the two-dimensional graph, displaying on a graphical user interface one or more selected datasets plotted on a two-dimensional graph in the viewable time frame, displaying on the graphical user interface one or more graphical elements representing events at locations proximate the two-dimensional graph when the events occurred in the viewable time frame, allowing a user to use the input interface to switch to a list view from the two-dimensional graph and displaying on the graphical user interface the list view including a chronological list of events corresponding to at least a portion of the viewable time frame of the two-dimensional graph.

In one or more exemplary embodiments, the at least one event may include one of filter set changes, logins, log accesses, screen locks, settings changes, bag changes, anticoagulation advisories, alarms, battery charge levels, system voltages (voltage changes or thresholds), viewing of screens (screen views), configuration changes, exporting of data (data exports), prescription changes, nurse calls, help accesses, and self tests.

In one or more exemplary embodiments, the graphical user interface may be further configured to depict an event type selection region and the computing apparatus may be further configured to execute or the method may further include displaying an event type selection region on the graphical user interface, allowing a user to use the input interface to select one or more event types of a plurality of different event types using the event type selection region of the graphical user interface, and displaying on the graphical user interface one or more graphical elements representing events of the one or more selected event types at locations proximate the two-dimensional graph (e.g., located below the time axis of the two-dimensional graph, etc.) when the events occurred in the viewable time frame. In at least one embodiment, the one or more graphical elements representing events of each selected event type of the one or more selected event types may include at least one different characteristic than the one or more graphical elements representing events of different selected event types of the one or more selected event types. Further the computing apparatus may be further configured to execute or the method may further include allowing a user to use the input interface to select a specific event by selecting a graphical element of the one or more graphical elements representing events and displaying an event information area including information relevant to the selected specific event. In at least one embodiment, the computing apparatus may be further configured to execute or the method may further include allowing a user to use the input interface to switch to a list view by selecting a list view icon.

In one or more exemplary embodiments, the graphical user interface may be further configured to depict a list view that may include a chronological list of events. Further, the computing apparatus may be further configured to execute or the method may further include allowing a user to use the input interface to switch to a list view and displaying the list view including a chronological list of events corresponding to at least a portion of the viewable time frame of the two-dimensional graph. In at least one embodiment, the computing apparatus may be further configured to execute or the method may further include displaying a list view icon in the event information area and allowing a user to use the input interface to switch to a list view using the list view icon. In at least one embodiment, the computing apparatus may be further configured to execute or the method may further include allowing a user to use the input interface to scroll through the chronological list of events and select one or more specific events and allowing a user to return to the two-dimensional graph. The viewable time frame of the two-dimensional graph may shift to a time period in which the selected specific event occurred (e.g., the selected time interval may remain unchanged.).

In one or more embodiments, the computing apparatus may be further configured to execute or the method may further include allowing a user to use the input interface to adjust the viewable time frame from the selected time interval and displaying an indication on the graphical user interface proximate the two-dimensional graph indicating that the viewable time frame is different than the selected time interval. In at least one embodiment, the indication on the graphical user interface proximate the two-dimensional graph indicating that the viewable time frame is different than the selected time interval may include at least one change in a characteristic of the outline of the two-dimensional graph.

In one or more exemplary embodiments, the graphical user interface may be further configured to depict a dataset selection region and the computing apparatus may be further configured to execute or the method may further include displaying on the graphical user interface a plurality of different dataset icons in a dataset selection region, where each dataset icon of the plurality of different dataset icons corresponds to a different dataset of a plurality of different datasets, allowing a user to use the input interface to select one or more datasets by selecting one or more dataset icons using the dataset selection region of the graphical user interface, and displaying on the two-dimensional graph the one or more selected datasets.

In one or more exemplary embodiments, the graphical user interface may be further configured to depict a data type selection region and the computing apparatus may be further configured to execute or the method may further include displaying on the graphical user interface a plurality of different data type icons in a data type selection region, where each data type icon of the plurality of different data type icons corresponds to a different data type of a plurality of different data types, allowing a user to use the input interface to select one or more data types by selecting one or more data type icons using the data type selection region, and displaying on the two-dimensional graph one or more datasets of the one or more selected data types.

In one or more embodiments, the computing apparatus may be further configured to execute or the method may further include allowing a user to use the input interface to scroll through the chronological list of events when in list view and select a specific event and allowing a user to return to the two-dimensional graph from the list view. The viewable time frame of the two-dimensional graph may shift to a time period in which the selected specific event occurred.

The above summary of the present disclosure is not intended to describe each embodiment or every implementation thereof. Advantages, together with a more complete understanding of the present disclosure, will become apparent and appreciated by referring to the following detailed description and claims taken in conjunction with the accompanying drawings.

DETAILED DESCRIPTION OF EXEMPLARY EMBODIMENTS

Figure 1:
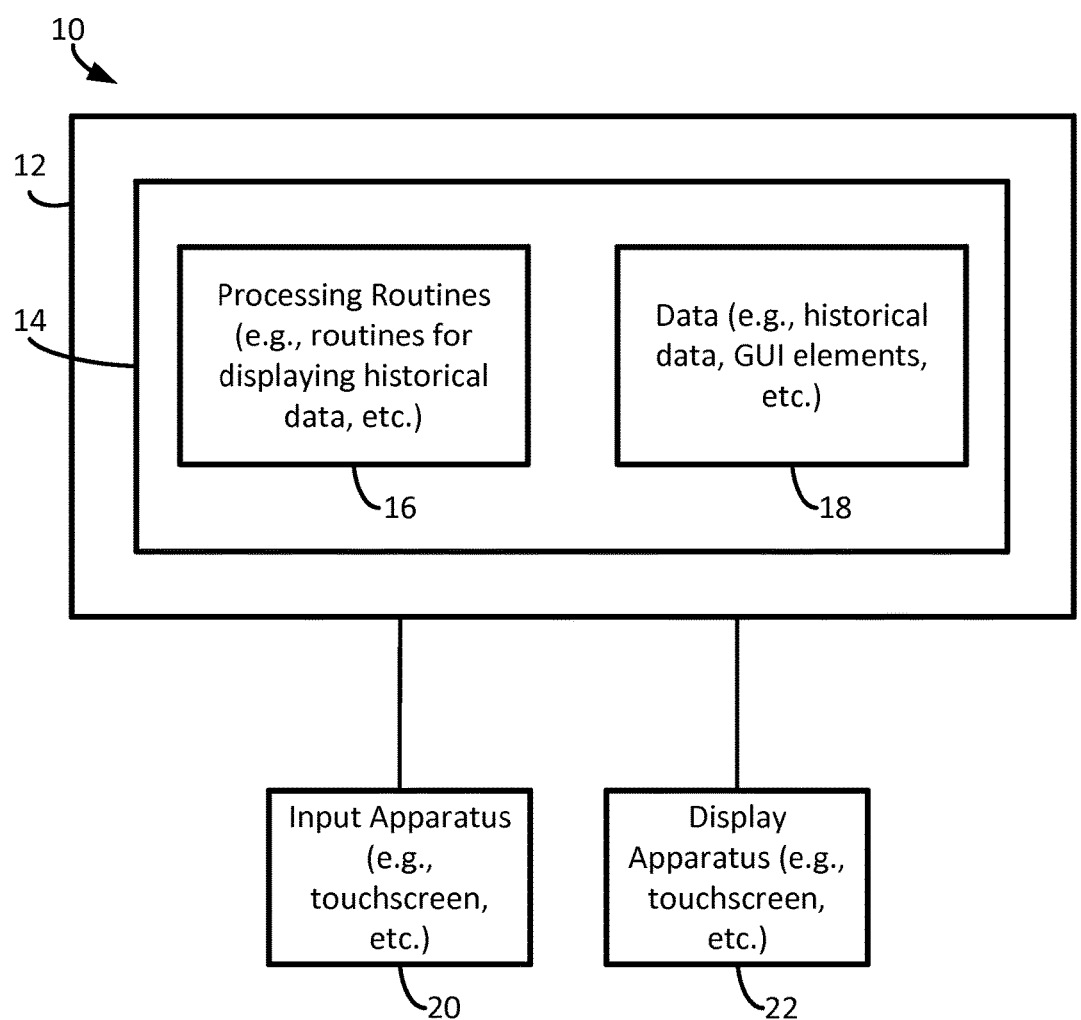
FIG. 1 is a block diagram of an exemplary extracorporeal blood treatment system including input apparatus and display apparatus that may utilize the user interfaces and methods described herein.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods of selecting, viewing, and filtering historical data for extracorporeal blood treatments shall be described with reference to FIGS. 1-21. Extracorporeal blood treatment systems may log, or store, one or more parameters and/or events of one or more extracorporeal blood treatments resulting in historical data. The exemplary systems and methods described herein provide graphical user interfaces to display such historical data. Generally, the historical data may include patient fluid removal data, fluids data, treatment data, anticoagulation data, pressure data, event data, settings data, patient data, alarm data, system voltage and current data, system timing data, user interaction data (e.g., interactions with the user interface such as button presses and screen selection), etc.

The patient fluid removal data may include total patient fluid removal data, unintended patient fluid removal data, selected limit data (e.g., selected limits for unintended patient fluid gain/loss over a selected period such as 1 hour, 3 hours, or 24 hours), target effluent data, target patient plasma loss data, plasma volume exchange data, etc. The fluids data may include pre blood pump data, dialysate data, replacement fluid post filter data, effluent data, filtration fraction data, predilution data, rate per patient kilogram data, ultrafiltration rate data, ultrafiltration rate post % of blood flow rate data, etc. The treatment data may include prescribed effluent dose data, delivered effluent dose data, target effluent dose data, prescribed ultrafiltration rate (UFR) dose data, target UFR dose data, delivered UFR dose data, etc. The anticoagulation data may include estimated patient citrate load data, citrate solution data, calcium solution data, replacement solution data, calcium compensation data, syringe volume delivery data, bolus delivery data, etc. The pressure data may include access line pressure data, return line pressure data, filter pressure data, transmembrane pressure (TMP) data, pressure drop across the filter (P DROP) data (e.g., the pressure conditions in the blood compartment of a filter), self-test data, pressure alarm data, disconnect and occlusion limit data, stabilization pressure data, etc. The event data may include system configuration data, alarm data, settings data, therapy set data, advisory data, prescription settings data, system settings data, anticoagulation data, pressure data, patient data, mechanical data, dose data, etc.

An exemplary extracorporeal blood treatment system 10 depicted in FIG. 1 may be used to execute the exemplary methods and/or processes described herein. In at least one embodiment, the system 10 may be a machine for the extracorporeal treatment of blood. The system 10 could, for example, alternatively be a blood processing device or a blood component preparation device or other medical apparatus for fluid delivery and/or collection.

As shown, the exemplary extracorporeal blood treatment system 10 includes computing apparatus 12. The computing apparatus 12 may be configured to receive input from input apparatus 20 and transmit output to display apparatus 22. Further, the computing apparatus 12 may include data storage 14. Data storage 14 may allow for access to processing programs or routines 16 and one or more other types of data 18 that may be employed to carry out exemplary methods and/or processes for use in performing extracorporeal blood treatment, logging historical data, filtering historical data, and displaying historical data. For example, the computing apparatus 12 may be configured to log, or record, data such as flow rates and volumes, to allow a user to select and view various sets of the historical data using the input apparatus 20 (e.g., based on input from the user), and to display the user-selected historical data using the display apparatus 22 (e.g., which will be described further herein with respect to FIGS. 4-21).

The computing apparatus 12 may be operatively coupled to the input apparatus 20 and the display apparatus 22 to, e.g., transmit data to and from each of the input apparatus 20 and the display apparatus 22. For example, the computing apparatus 12 may be electrically coupled to each of the input apparatus 20 and the display apparatus 22 using, e.g., analog electrical connections, digital electrical connections, wireless connections, bus-based connections, etc. As described further herein, a user may provide input to the input apparatus 20 to manipulate, or modify, one or more graphical depictions (e.g., windows, regions, areas, buttons, icons, etc.) displayed on the display apparatus 22 to select and/or display historical data.

Further, various devices and apparatus may be operatively coupled to the computing apparatus 12 to be used within the computing apparatus 12 to perform one or more extracorporeal procedures/treatments as well as the functionality, methods, and/or logic described herein. As shown, the system 10 may include input apparatus 20 and display apparatus 22. The input apparatus 20 may include any apparatus capable of providing input to the computing apparatus 12 to perform the functionality, methods, and/or logic described herein. For example, the input apparatus 20 may include a touchscreen (e.g., capacitive touchscreen, a resistive touchscreen, a multi-touch touchscreen, etc.), a mouse, a keyboard, a trackball, etc. The input apparatus 20 may allow a user to select and filter various historical data to be viewed on the display apparatus 22 (e.g., displaying a graphical user interface depicting historical data).

Likewise, the display apparatus 22 may include any apparatus capable of displaying information to a user, such as a graphical user interface, etc., to perform the functionality, methods, and/or logic described herein. For example, the display apparatus 22 may include a liquid crystal display, an organic light-emitting diode screen, a touchscreen, a cathode ray tube display, etc. In at least one embodiment, touchscreen apparatus may be overlaid on a display screen allowing a user to touch graphical buttons and icons on the display screen to enable specific actions to occur, or take place. As described further herein, the display apparatus 22 may be configured to display a graphical user interface that includes one or more regions and/or areas used to select and display historical data for an extracorporeal blood treatment. For example, the graphical user interface displayed by the display apparatus 22 may include, or display, a two-dimensional graph, datasets plotted on the two-dimensional graph, one or more graphical elements, or icons, representing events proximate the two-dimensional graph, a time interval selection region, an event type selection region, an event list region or view, event information areas, a historical data region, an event display region, etc. Each graph, region, view, button, icon, panel, area, dialog, etc. may be used by a user to select and view historical data on the graphical user interface of the display apparatus 22. As used herein, a "region" of a graphical user interface may be defined as a portion of the graphical user interface within which information may be displayed or functionality may be performed. Regions may exist within other regions, may be displayed separately or simultaneously, etc. For example, smaller regions may be located within larger regions, regions may be located side-by-side, etc. Additionally, as used herein, an "area" of a graphical user interface may be defined as a portion of the graphical user interface located with a region that is smaller than the region it is located within.

The processing programs or routines 16 may include programs or routines for performing computational mathematics, matrix mathematics, standardization algorithms, comparison algorithms, or any other processing required to implement one or more exemplary methods and/or processes described herein. Data 18 may include, for example, historical data, user accounts, licensing information, treatment profiles, bitmaps, videos, calibration data, system configuration information, solutions data, engineering logs, event and alarm data, system pressures, system voltages, system currents, self-test sequence data, user interaction data, treatment state data, monitor usage data, utilization data, software executables, patient information, treatment summary info, treatment run time data, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the system 10 may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The program used to implement the methods and/or processes described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the system 10 may be implemented using a computer readable storage medium, configured with a computer program, where the storage medium so configured causes the computer to operate in a specific and predefined manner to perform functions described herein. Further, in at least one embodiment, the system 10 may be described as being implemented by logic (e.g., object code) encoded in one or more non-transitory media that includes code for execution and when executed by a processor operable to perform operations such as the methods, processes, and/or functionality described herein.

Likewise, the system 10 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data).

The computing apparatus 12 may be, for example, any fixed or mobile computer system (e.g., a controller, a microcontroller, a personal computer, mini computer, etc.). The exact configuration of the computing apparatus 12 is not limiting, and essentially any device capable of providing suitable computing capabilities and control capabilities (e.g., graphics processing, control of extracorporeal blood treatment apparatus, etc.) may be used.

As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 12 described herein.

Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow users to select and filter various historical data to be displayed on the display apparatus.

The methods and/or logic described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, or other devices. The term "processor" or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions and/or logic on a computer-readable medium such as RAM, ROM, NVRAM, EEPROM, FLASH memory, magnetic data storage media, optical data storage media, or the like. The instructions and/or logic may be executed by one or more processors to support one or more aspects of the functionality described in this disclosure.

The exemplary systems, and exemplary methods performed, or used, by such exemplary systems, described herein for selecting and viewing of historical data in extracorporeal blood treatment may be generally referred to as dialysis systems. The general term dialysis as used herein includes hemodialysis, hemofiltration, hemodiafiltration, hemoperfusion, liver dialysis, and therapeutic plasma exchange (TPE), among other similar treatment procedures. In dialysis generally, blood is taken out of the body and exposed to a treatment device to separate substances therefrom and/or to add substances thereto, and is then returned to the body. Although extracorporeal blood treatment systems capable of performing general dialysis (as defined above, including TPE) shall be described herein with reference to the exemplary extracorporeal blood treatment system of FIGS. 2-3, other systems such as those for infusion of drugs, performance of continuous renal replacement therapy (CRRT), extracorporeal membrane oxygenation (ECMO), hemoperfusion, liver dialysis, apheresis, TPE, etc. may benefit from the systems, methods, and apparatus described herein and the present disclosure is not limited to any particular fluid processing system.

Figure 2:
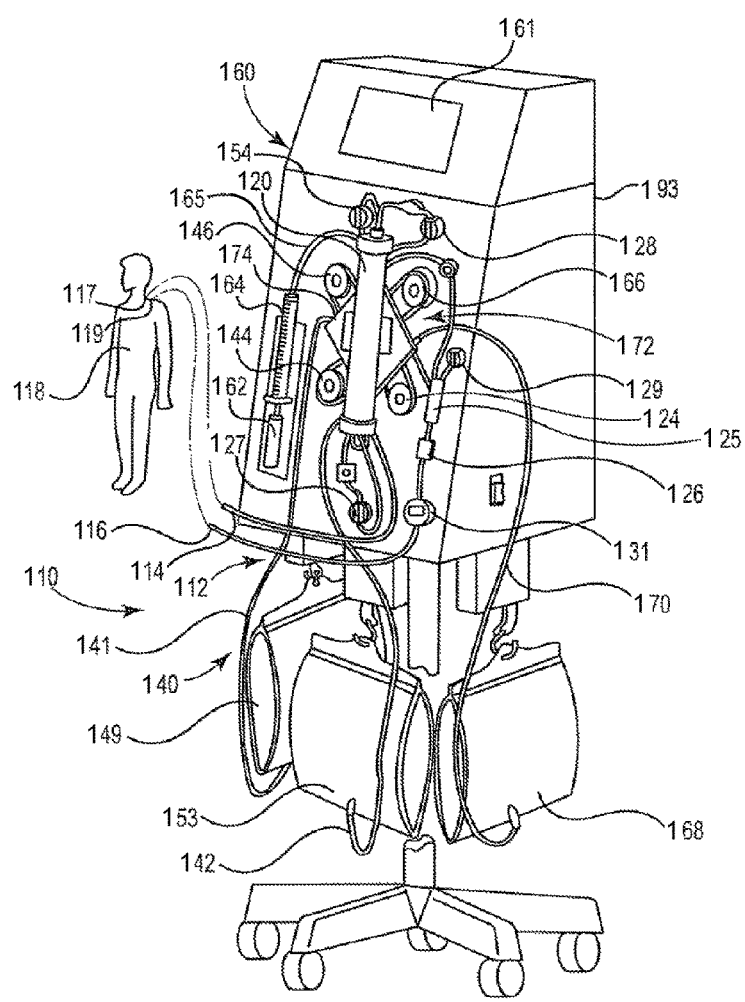
FIG. 2 is a perspective illustration of an exemplary fluid processing system that may include a graphical user interface as described herein.
Figure 3:
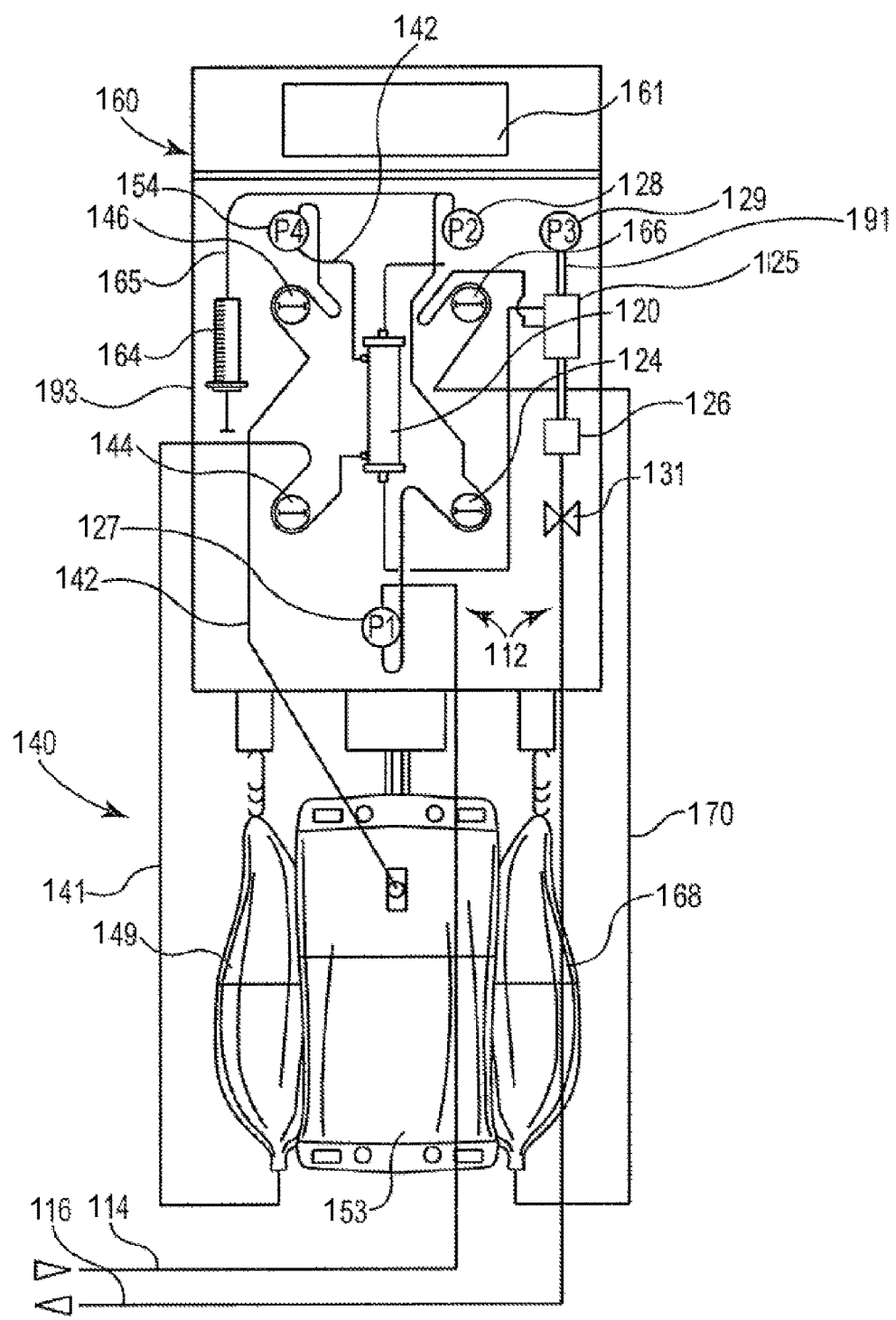
FIG. 3 is a front view of a portion of the exemplary fluid processing system shown in FIG. 2.

In the perspective and partial front views of FIGS. 2-3, the exemplary extracorporeal blood treatment system 110 that may implement the graphical user interfaces as described herein generally includes a blood tubing circuit 112 having first and second tubing segments 114 and 116 which are both connected to the vascular system of a patient 118 via access and return devices 117 and 119, respectively. Devices 117 and 119 may be cannulas, catheters, winged needles or the like as would be understood by one skilled in the art. Tubing segments 114 and 116 are also connected to a filtration or processing unit 120. In dialysis, filtration unit 120 is a dialyzer, which is also often referred to as a filter. In TPE, it may also be referred to as a plasma filter. In this exemplary system 110, a peristaltic pump 124 is disposed in operative association with the first tubing segment 114. Numerous other component devices of blood circuit 112 are also included as, for example, pressure sensors 127, 128.

Also shown in FIGS. 2-3 is the processing fluid or filtrate side of system 110 which generally includes a processing fluid circuit 140 having first and second processing fluid tubing segments 141 and 142. Each of these tubing segments is connected to the filtration unit 120. In these FIGS. 2-3, a respective fluid pump 144, 146 is operatively associated with each of these tubing segments 141 and 142. First tubing segment 141 is also connected to a processing fluid source (e.g., fluid bag 149), which may include electrolytes premixed therein. Second tubing segment 142 is connected to a waste collection device (e.g., a waste container such as a bag 153). A pressure sensor 154 may also be disposed in second dialysis fluid tubing segment 142.

FIGS. 2-3 show a system that is common as a basic model for numerous dialysis procedures including TPE. Additional fluid lines, circuits, and components may be added (or deleted) to increase therapy options. Further, as shown in FIGS. 2-3, the system 110 includes an extracorporeal blood control apparatus 160 that provides numerous treatment options, which may be controlled and/or monitored via the control/display screen 161 (e.g., a control apparatus or controller provided in a system housing 193). Touch-screen controls may be incorporated herewith and/or other conventional knobs or buttons (not shown) may be used (e.g., graphical user interfaces may be displayed via a touchscreen as described herein). Other and more detailed information regarding an example apparatus 160 may be found in U.S. Pat. No. 5,679,245; U.S. Pat. No. 5,762,805; U.S. Pat. No. 5,776,345; and U.S. Pat. No. 5,910,252; inter alia.

A general dialysis treatment procedure as performed, for example, with an apparatus described with reference to FIGS. 2-3 will be generally described for exemplary purposes. First, blood is removed from the patient 118 via access device 117 by, e.g., the blood pump 124, and flows through access line 114 to the filter 120. Filter 120 processes this blood according to a selected one or more of a number of extracorporeal blood treatment profiles (e.g., selected and controlled via screen interface 161 of control apparatus 160) and then returns the processed or treated blood to the patient 118 through return line 116 and return device 119 inserted in or otherwise connected to the vascular system of the patient 118. The blood flow path to and from the patient 118, which includes the access device 117, the access line 114, the blood pump 124, the filter 120, as well as the return line 116 and return device 119 back to the patient, forms the blood flow circuit 112.

Pressure sensors may be used to sense various pressures in the system 110. For example, the pressure sensor 127 may be connected in the access line 114 and allow the fluid pressure in the access line 114 to be monitored and the second pressure sensor 128 may be connected in the blood circuit 112 between the first pump 124 and the blood entrance into the filter 120 and may be used to detect and monitor the pressure of the blood supplied to the entrance of the filter 120.

The system 110 may further include a deaeration chamber 125 in the return line to provide a conveyance path that operates like a vortex to propel air out of the blood. Post-filter replacement solution may be added into the deaeration chamber on the top of the blood to prevent an air/blood interface. A deaeration chamber monitor line 191 may connect the deaeration chamber 125 to an internal pressure transducer within the system housing 193 using a connection apparatus, such as, for example, a return pressure port 129. This enables return pressure monitoring, and removal of air from the deaeration chamber, if needed. A return clamp 131 connected in the blood circuit 112 selectively allows or terminates the flow of blood through the blood circuit 112 (e.g., return clamp 131 may be activated whenever air is detected in the blood by bubble detector 126). Further, a pump 162 may be connected to an anticoagulant container 164 to deliver anticoagulant through an anticoagulant line 165 to the blood in tubing segment 114 and a pump 166 may deliver replacement fluid from a replacement fluid container or bag 168 through a replacement fluid line 170.

The secondary flow circuit 140 is also shown in FIGS. 2-3 as it interacts with filter 120. The secondary flow circuit 140 is connected to the secondary chamber of filter 120. Matter extracorporeally removed from the blood is removed from the secondary chamber of filter 120 through the outlet tubing segment 142 of the secondary flow circuit 140, and matter extracorporeally added to the blood is moved into filter 120 through inlet tubing segment 141 of the secondary flow circuit 140. The secondary flow circuit 140 generally includes the fluid source such as bag 149, inlet fluid line 141, third peristaltic pump 144, the secondary chamber of the filter 120, a waste fluid line 142, pressure sensor 154, fourth pump 146, and the waste collection device such as container 153. The source fluid bag 149 may contain a sterile processing fluid, generally isotonic to blood, into which blood impurities will diffuse through the semi-permeable membrane of the filtration unit 120. The pump 144 is connected in inlet fluid line 141 for delivering processing fluid from the processing fluid source 149 into an entrance to the filter 120. The waste collection container 153 is provided to collect or receive matter from the blood transferred across the semi-permeable membrane in filter 120 and/or to receive the used processing fluid after it has passed through the filter 120. The fourth pump 146 is connected to the waste collection line 142 for moving body fluid from the filter 120 into the waste collection container 153. The pressure sensor 154 may also be located in the waste collection line 142 for the purpose of monitoring the pressure in the secondary chamber of filter 120.

The filtration unit 120, the flow tubing lines, and the other components in the primary and secondary flow circuits 112 and 140 described herein (with the exception, for example, of the pumps and perhaps a few other items) may be formed as an integral, replaceable unit (e.g., an extracorporeal blood set). This integral replacement unit may be referred to herein as a "therapy set." An example of such a therapy set, or integral replaceable unit, is described in greater detail in U.S. Pat. No. 5,441,636 entitled Integrated Blood Treatment Fluid Module (see also, U.S. Pat. No. 5,679,245, entitled Retention Device for Extracorporeal Treatment Apparatus). Any number of therapy sets for use in performing different therapies may be available depending on the system configuration.

As can generally be appreciated from FIGS. 2-3, the integrated tubing and filter module (identified by the reference numeral 172) includes the filter 120 and all the tubing and related components described above which are connectable to apparatus 160. For example, the filter and tubing may be retained on a plastic support member 174 which is, in turn, connectable to apparatus 160 (e.g., connectable to the system housing 193 of the apparatus 160). When in the operative position connected to apparatus 160, flexible fluid conducting tubing lines to and from the filtration unit 120 are held in operative, pump communicative loops for operative contact with the peristaltic pumping members of the pumps 124, 144, 146 and 166 to cause the fluid to flow through the primary (blood) and secondary (processing fluid) circuits 112 and 140. Module 172, including filter 120 and all the tubing lines and associated flow components may be disposable after use. The peristaltic pumping members of pumps 124, 144, 146, and 166 may be fixedly disposed on apparatus 160 (without the disposable tubing loop components) and may be re-usable. In general, electrical, mechanical, or electromechanical components are also fixedly disposed in or on apparatus 160 (e.g., connectable to the system housing 193 of the apparatus 160). Examples of such components include the display screen 161 (e.g., a touchscreen), the bubble detector 126, line clamps 131 and connection apparatus for coupling to pressure sensor apparatus used to implement pressure sensors 127, 128, 154, etc.

Screenshots depicting exemplary graphical user interfaces for selecting and viewing historical data are depicted in FIGS. 4-21. Such exemplary graphical user interfaces may be depicted by the display apparatus 22 of the system 10 described herein with reference to FIG. 1 and/or the display screen 161 of FIGS. 2-3. Additionally, the graphical user interfaces described herein may be depicted on a touch-screen, and in such configuration, the input apparatus would also be the touchscreen.

Figure 4:
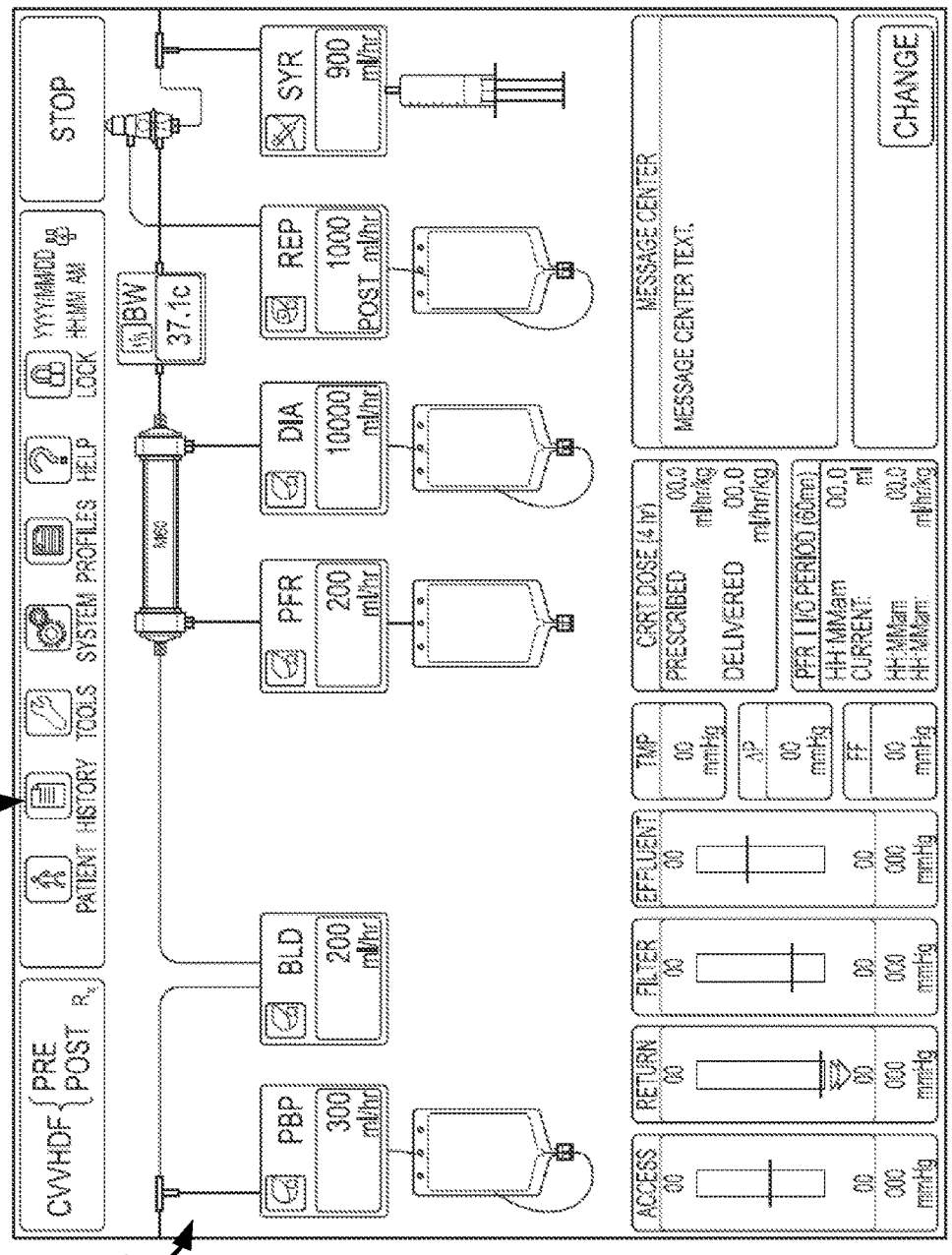
FIG. 4 is a screenshot of an exemplary graphical user interface of extracorporeal blood treatment systems, for example, such as shown generally in FIGS. 1-3.
Figure 5:
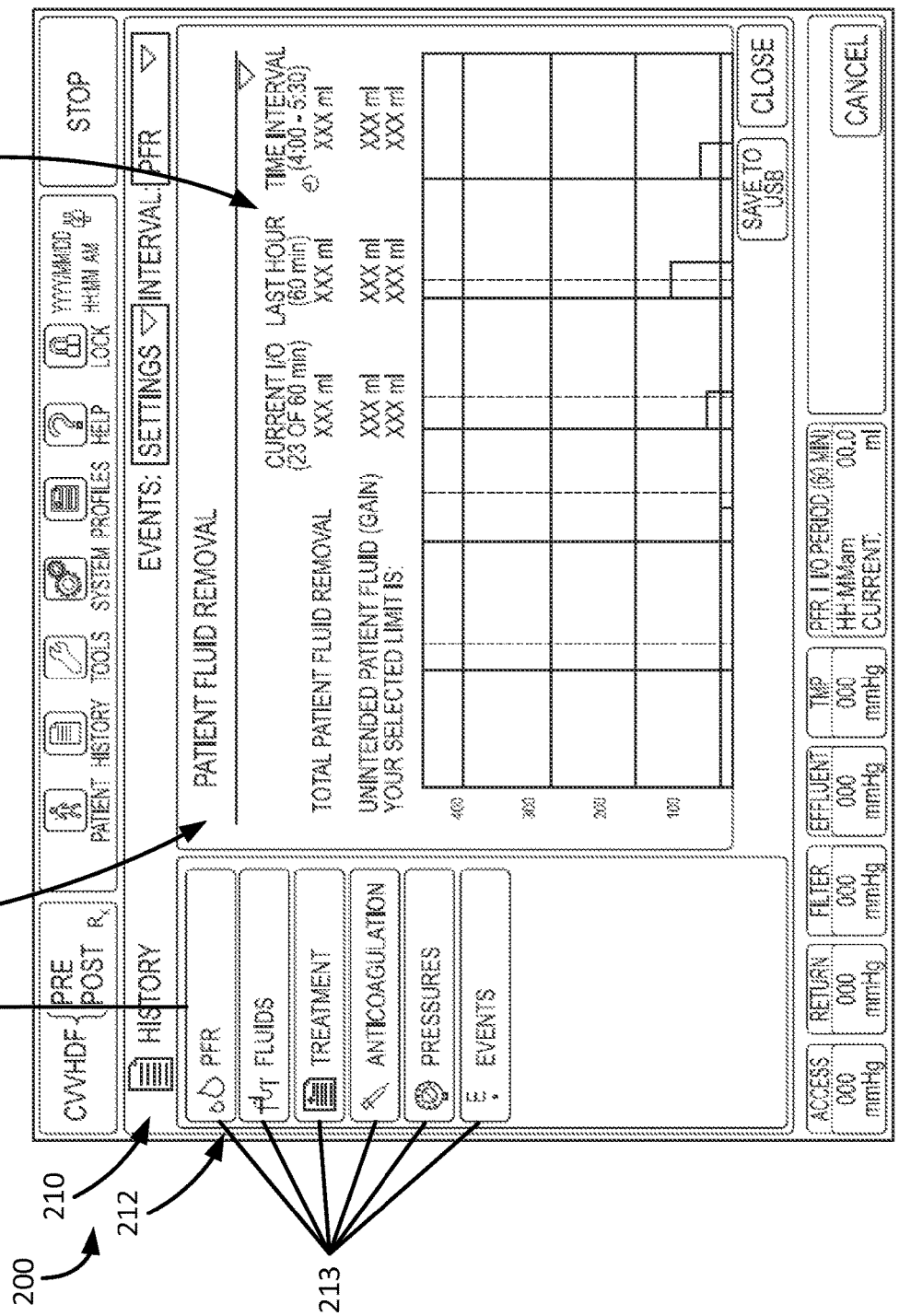
FIGS. 5-15 and 20-21 are screenshots of exemplary graphical user interfaces for displaying historical data along a two-dimensional graph for use in extracorporeal blood treatment systems, for example, such as shown generally in FIGS. 1-3.

An exemplary graphical user interface 200 is depicted in FIG. 4 that may be generally used during an extracorporeal blood treatment. The graphical user interface 200 as shown in FIG. 4 may include a fluid circuit region 201 depicting a fluid circuit used to deliver an extracorporeal blood treatment. The graphical user interface 200 may further include, among other things, a "History" area, or button, 202 that, when selected by a user, may display a historical data graphical user interface 210 as depicted in FIG. 5.

The historical data graphical user interface 210 of the graphical user interface 200 includes a data type selection region 212 depicted on the left side of the historical data graphical user interface 210 and a historical data region 220 depicted on the right side of the historical data graphical user interface 210. The data type selection region 212 may include a plurality of different data type areas, or icons, 213 such as "PFR" (i.e., patient fluid removal), "Fluids," "Treatment," "Anticoagulation," "Pressures," and "Events." When a data type area, or icon, 213 has been selected in data type selection region 212, the historical data depicted in the historical data region 220 may correspond to the selected data type area 213. For example, if the PFR data type area of the data type areas 213 is selected, patient fluid removal historical data may be depicted in the historical data region 220. Further, for example, if the Fluids data type area of the data type areas 213 is selected, historical data relating to fluids may be depicted in the historical data region 220. Additionally, the data type area 213 that is selected may be highlighted as shown by highlight 214. As shown in FIG. 5, the PFR data type area of the data type areas 213 is currently selected, and thus, patient fluid removal data is depicted in the historical data region 220.

The patient fluid removal data depicted in the historical data region 220 may include any data related to patient fluid removal such as, e.g., volumes, masses flow rates, make-up time, make-up volume, etc. of total patient fluid removal, unintended patient fluid (gain), selected limits, etc. over various time periods such as, e.g., the current input/output (I/O) period (e.g., an I/O period may be defined as an operator, or user, controlled time period setting that may be, e.g., 15 minutes, 30 minutes, 40 minutes, 50 minutes, 1 hour, 2 hours, 4 hours, etc. to chart fluid moving "in" and "out" of a patient), the last, or previous, hour, a specific time interval, a duration of a treatment set, the duration of a treatment, the duration of a nurse or operator shift, the duration of an alarm, etc. Additionally, the patient fluid removal data depicted in the historical data region 220 may be depicted alphanumerically (e.g., amount of ml) in an alphanumeric data region 222 and/or graphically (e.g., using line or bar graphs).

Figure 6:
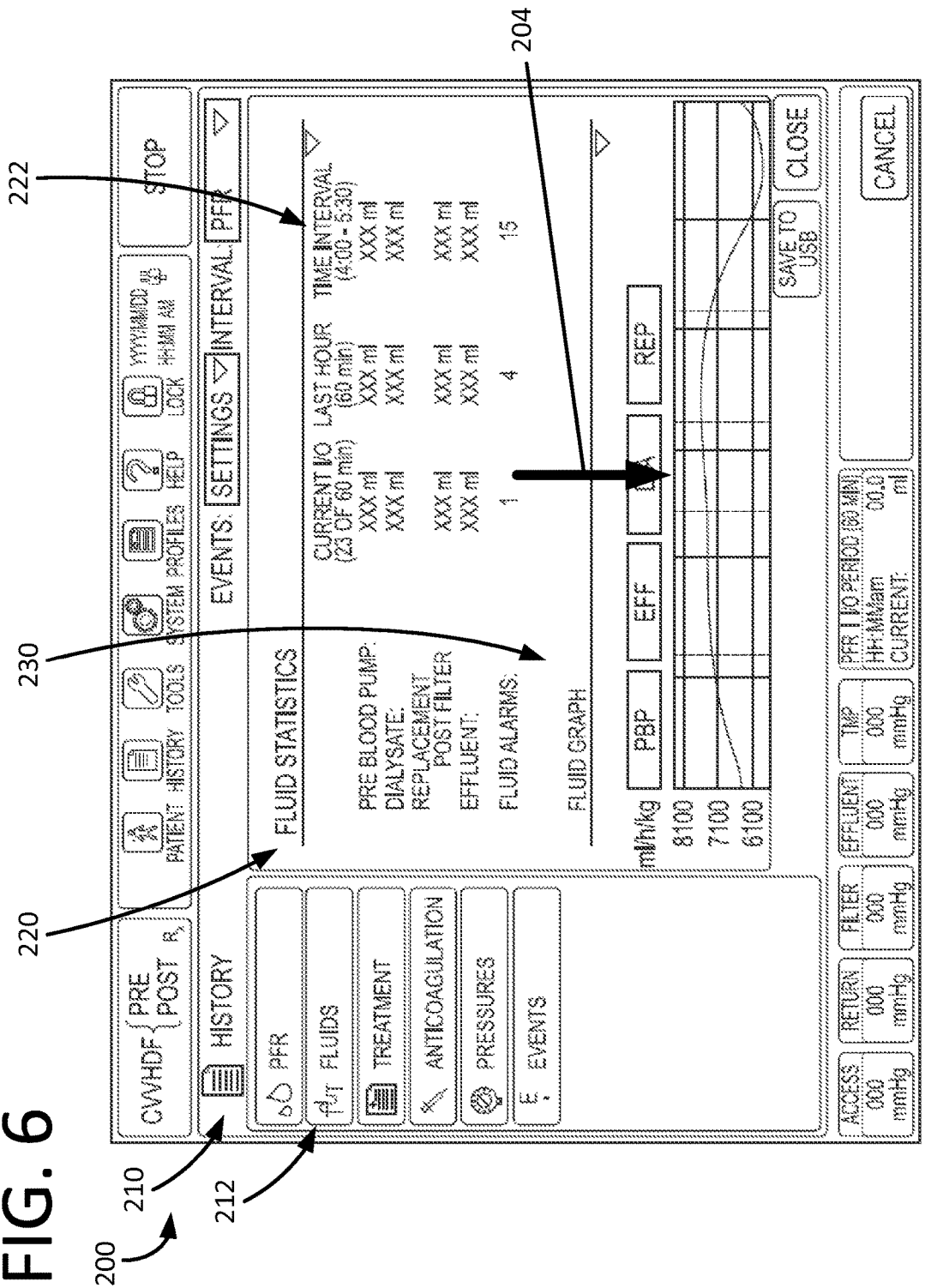

The "Fluids" data type area 213 has been selected in data type selection region 212 in FIG. 6, and as such, the historical data depicted in the historical data region 220 may include fluids data. For example, as shown in FIG. 6, fluids data depicted in the historical data region 220 may include any fluid data related to an extracorporeal blood treatment that is being performed, or was performed, such as, e.g., volumes, masses flow rates, fluid alarms, filtration fraction, predilution data, rate per patient kilogram, UFR, UFR post % of BFR, prescribed dose data, target dose data, delivered dose data, etc. of pre blood pump, dialysate, replacement rate, effluent, blood flow rate, ultrafiltration, anticoagulation (or syringe), etc. over various time periods such as, e.g., the current input/output (I/O) period, the last, or previous, hour, a time interval, a duration of one or more treatment sets, a duration of one or more treatments, a duration of one or more nurses shifts, a duration of one or more alarms, etc.

Figure 7:
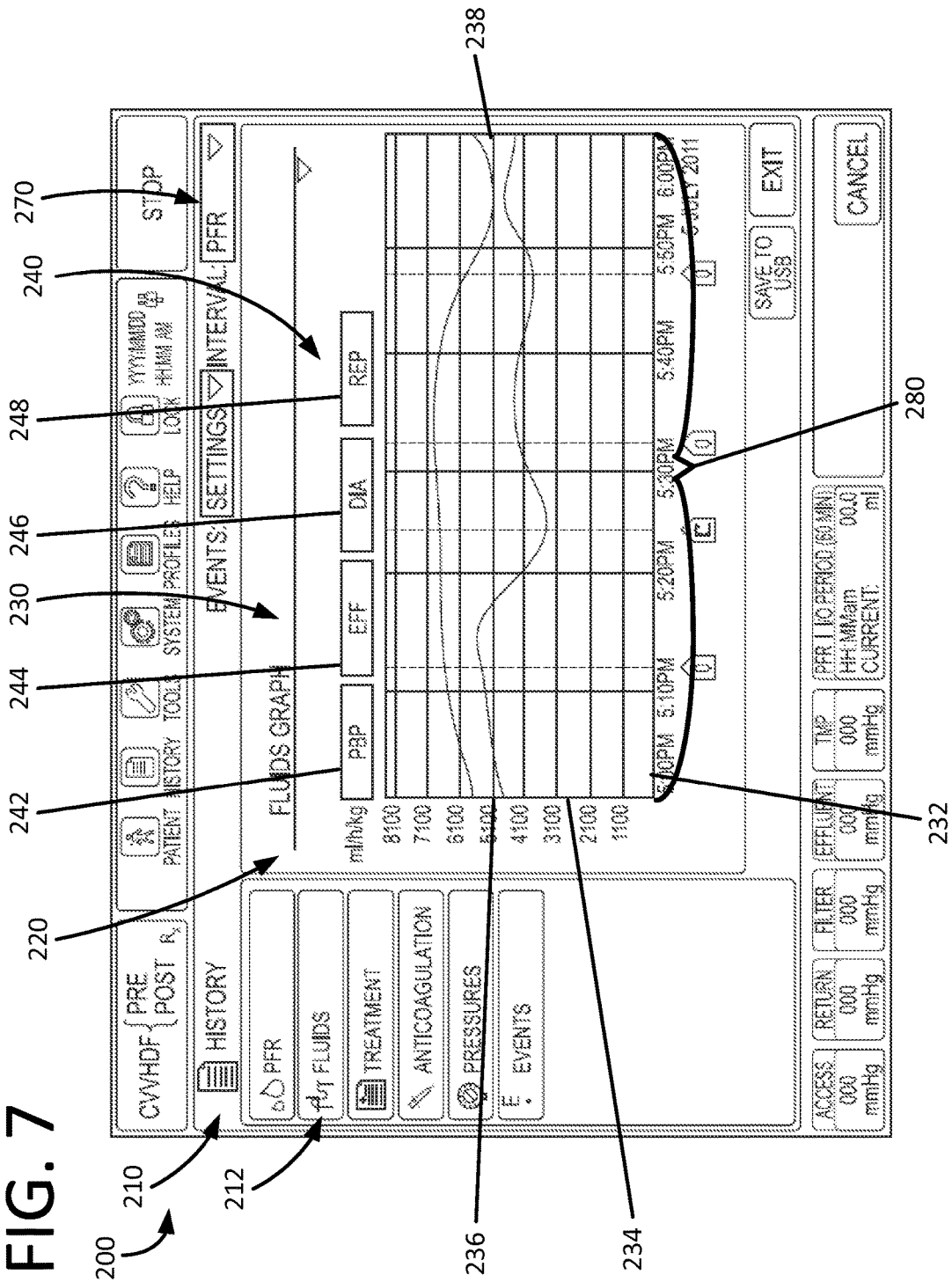

Additionally, the fluids data depicted in the historical data region 220 may be depicted alphanumerically (e.g., masses, volumes, flow rates, etc.) and/or graphically (e.g., using line or bar graphs). For example, a portion of a two-dimensional graph 230 entitled "Fluid Graph" is depicted in the historical data region 220 as shown in FIG. 6. As user may scroll the historical data region 220 downwardly as represented by arrow 204 to view the entire two-dimensional graph 230. When the input apparatus is a touchscreen, a user may touch the touchscreen and swipe upwardly (or downwardly) to scroll the historical data region 220 to, e.g., view the entire two-dimensional graph 230. As shown in FIG. 7, a user has scrolled upwardly (or downwardly) to expose, or display, the entire two-dimensional graph 230. Further, the current position of the window may be indicated to the user by using a scroll bar to the right of the scrollable window.

The two-dimensional graph 230 may include, or define a time axis 232 representing time (e.g., the x-axis) and a value axis 234 (e.g., the y-axis) extending relative to the time axis 232 and representing at least one value. Additionally, the two-dimensional graph 230 may define a viewable time frame 280 extending from a first end region 236 to a second end region 238 parallel to, or along, the time axis 232. A user may traverse, or move, the viewable time frame 280 along the time-axis 232 to view a different period of time within the viewable time frame 280 by, e.g., touching the two-dimensional graph 230 and swiping left or right, selecting left or right movement areas (e.g., graphical arrows, etc.) depicted proximate the two-dimensional graph 230, etc. Further, if a user has changed to the viewable time frame 280 by viewing a different period of time than that set by selecting a time interval using the time interval selection region 270, an indication (e.g., at least one change in a characteristic of the two-dimensional graph 230) may be displayed in the historical data region 220 proximate the two-dimensional graph 230 indicating that the viewable time frame 280 is different than the selected time interval. For example, an outline of the two-dimensional graph may change color indicating that the viewable time frame 280 has been changed.

When a user switches to another data type (e.g., when selecting another data type area 213 in data type selection region 212), the viewable time frame 280 of the two-dimensional graph 230 for each data type may be kept the same. As such, a user may not lose track of the time period being displayed when switching between data types (and graphs depicting such data types). In other words, when a user changes the time interval using the time interval selection region 270 for one graph, the viewable time frame automatically changes for all other graphs. Thus, when a user switches from the "Fluids" data type to the "Pressures" data type, the same viewable time frame 280 for the graphs of the "Fluids" data type to the "Pressures" data type will be displayed. Additionally, a user may enable or disable this feature of allowing the viewable time frame 280 to remain constant across the graphs of each data type. For example, an area, or button, may be displayed proximate the graph 230 that allows a user to enable or disable this same viewable time frame feature.

One or more sets of data, or datasets, may be depicted on the two-dimensional graph 230 in the historical data region 220 individually or simultaneously. For example, flow rates (e.g., in ml/h), masses (e.g., in kilograms), and/or volumes (e.g., in ml) of fluids data such as pre blood pump, effluent, dialysate, replacement fluid, patient fluid, saline, glucose, anticoagulants such as, e.g., heparin or citrate, calcium containing fluids, albumin containing fluids, etc. may be depicted on the two-dimensional graph 230 individually or simultaneously.

A user may use input apparatus in conjunction with the display apparatus to display one or more datasets on the two-dimensional graph 230. For example, the historical data region 220 may include (e.g., may depict) a dataset selection region 240. The dataset selection region 240 may include a plurality of different dataset areas, or icons, representing different datasets of a plurality of different datasets such as "Fluids"-related datasets as shown in FIG. 7. As shown, the dataset selection region 240 includes a "PBP" area, or icon, 242 representing a pre blood pump flow rate dataset, an "EFF" area, or icon, 244 representing an effluent flow rate dataset, a "Dia" area, or icon, 246 representing a dialysate flow rate dataset, and a "REP" area, or icon, 248 representing a replacement fluid flow rate dataset.

Figure 8:
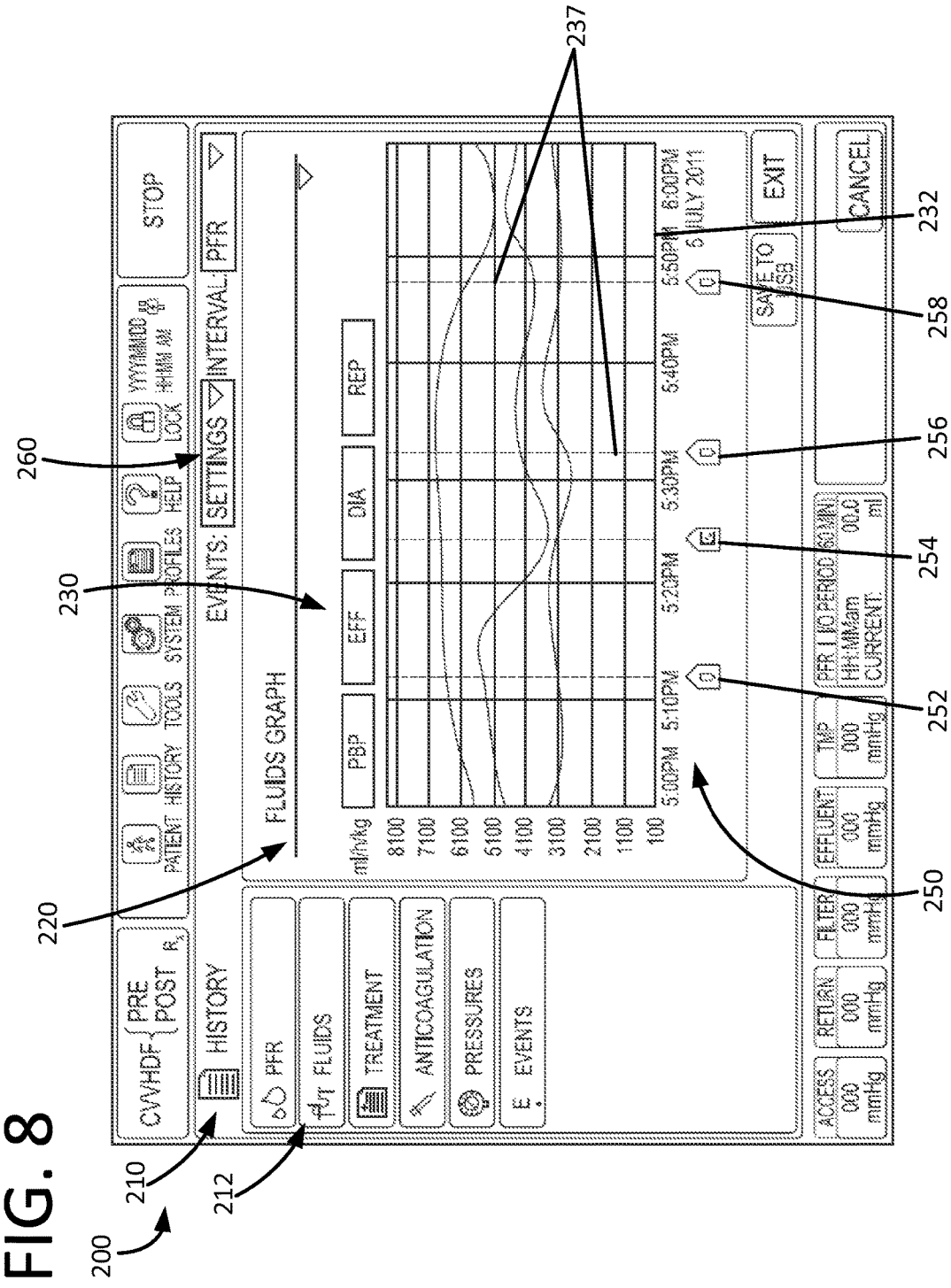

As shown in FIG. 7, two datasets, namely the pre-blood pump flow rate and the effluent flow rate datasets, are plotted, or depicted, in the two-dimensional graph 230. The graphical elements, or icons, 242, 244 representing the pre-blood pump flow rate and effluent datasets may be outlined as shown to signal, or indicate, that such datasets have been selected by a user. A user may select another dataset such as the dialysate flow rate dataset to be displayed (e.g., depicted or plotted on the two-dimensional graph 230) by selecting the "Dia" graphical element 246. As shown in FIG. 8, a user has selected the "Dia" icon 246 (e.g., in addition to the already selected PBP icon 242 and EFF icon 244 as shown in FIG. 7), and therefore, the two-dimensional graph 230 includes the pre-blood pump flow rate, effluent flow rate, and dialysate flow rate datasets. Although datasets of pre blood pump, effluent, dialysate, and replacement fluid are depicted in these exemplary figures, one of ordinary skill in the art will recognize any datasets related to extracorporeal blood treatment may also be depicted on the two-dimensional graph.

Events that may occur over the course of an extracorporeal blood treatment may also be depicted within or proximate to the two-dimensional graph 230 of the historical data region 220. Exemplary events may include alarms, settings changes, bag changes, logins, log accesses, screen locks, anticoagulation changes or advisories, therapy set changes, nurse changes, prescription changes, help accesses, self-tests, flow rate changes, dose changes, etc. As shown in FIG. 8, an exemplary event display region 250 is depicted below the two-dimensional graph 230. The event display region 250 includes one or more graphical elements representing events.

Each graphical element representing an event is located beneath the time axis 232 of the two-dimensional graph 230 at the time along the time axis 232 when the event occurred. As such, a user may be able to view one or more datasets such as fluid-related datasets depicted, or plotted, on the two-dimensional graph 230 while also viewing the events that occurred over the same time period (e.g., within the same viewable time frame 280). As shown, a reservoir (e.g., bag) graphical element, or icon, 252 representing a reservoir change is depicted between 5:10 pm and 5:20 pm, a flow element, or icon, 254 representing flow rate change is depicted between 5:20 pm and 5:30 pm, a reservoir graphical element, or icon, 256 representing reservoir change is depicted between 5:30 pm and 5:40 pm, and a reservoir graphical element, or icon, 258 representing reservoir change is depicted between 5:40 pm and 5:50 pm. Additionally, dotted lines 237 may extend upwardly within the two-dimensional graph 230 from each graphical element representing an event such that the moment in time which the event occurred may be more easily compared to the one or more datasets depicted in the two-dimensional graph 230

A user may desire, or want, to view events of a particular type (e.g., filter the type of events displayed). The historical data region 220 may include an event type selection region 260 located proximate the two-dimensional graph 230. The event type selection region 260 may allow a user using the input apparatus to select a type of event (e.g., one or more types of events) that should be depicted by graphical elements, or icons, proximate the two-dimensional graph 230 (e.g., filter the type of events displayed). As shown in FIG. 8, the "Settings" event type has been selected as indicated by the word "Settings" appearing in the event type selection region 260, and as such, only graphical elements representing events related to settings are displayed proximate the two-dimensional graph 230 in the event display region 250.

Figure 9:
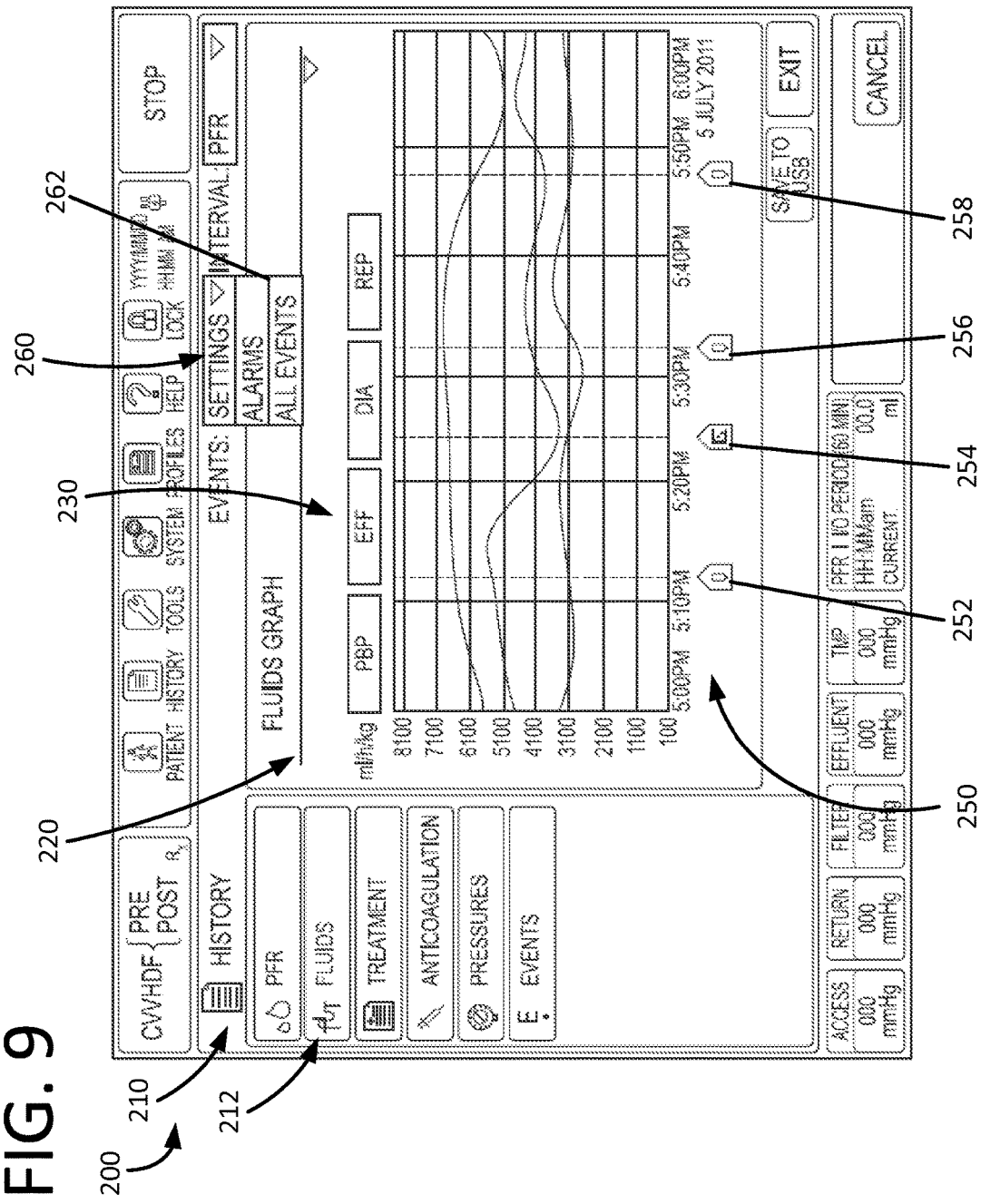

To change the event type displayed (e.g., in the event display region 250), a user may select the event type selection region 260 as shown in FIG. 9. After selecting the event type selection region 260, an event selection area 262 (e.g., menu, dialog, etc.) may be displayed including all the available event types as well as an "All Events" type. Although the exemplary methods and systems described herein may utilize, or include, more event types, as shown in FIG. 9, the displayed event types are "Settings," "Alarms," and "All Events." Further, although an exemplary event selection menu, or dialog, is depicted herein, it is to be understood that any graphical event selection graphic, or depiction, may be used by the exemplary methods and systems described herein (e.g., to filter the data being displayed).

Figure 10:
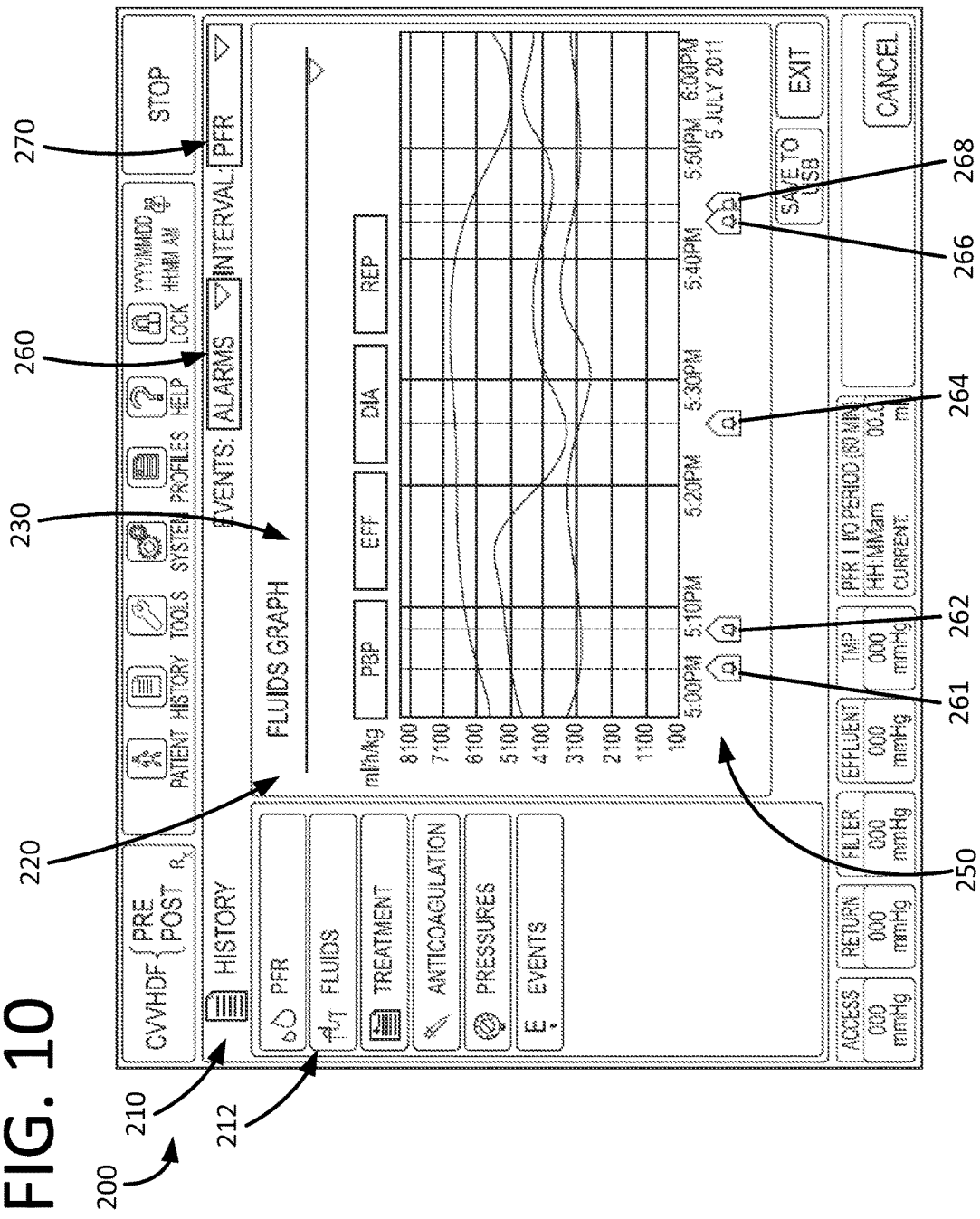

As shown in FIG. 10, the "Alarms" event type has been selected using the event type selection region 260. As a result, the "Settings" graphical elements, or icons, 252, 254, 256, 258 of FIG. 9 (e.g., the graphical elements representing events related to "settings") have been removed (e.g., disappeared, dismissed, etc.) from the event display region 250 of the historical data region 220 and the "Alarm" graphical elements, or icons, 261, 262, 264, 266, 268 (e.g., the graphical elements representing events related to "alarms") have been displayed in the event display region 250 of the historical data region 220. The "Alarms" graphical elements 261, 262, 264, 266, 268 may each represent an alarm that occurred within the viewable time frame 280 depicted in the two-dimensional graph 230. Further, the color of each alarm graphical element may vary depending on the severity of the alarm it represents. For example, if the alarm icon represents a high priority alarm such as, e.g., return line disconnection, the alarm icon may be red. Further, for example, if the alarm icon represents a low priority alarm such as, e.g., a reservoir change being required, the alarm icon may be yellow. Although only alarms are noted as being color coded, all events may be color coded. For example, graphical elements may be red for high priority alarms, orange for medium priority alarms, yellow for low priority alarms, green for user initiated events such as, e.g., a change in settings, and blue for machine initiated events, such as, e.g., elapsed timers and self-tests.

To, for example, distinguish between different types of events, the one or more graphical elements representing events of a selected event type of the one or more selected event types may include a different characteristic than the one or more graphical elements representing events of different selected event types. For example, the graphical elements 252, 254, 256, 258 representing settings may be different from (e.g., have different characteristics than) the graphical elements 261, 262, 264, 266, 268 representing alarms. As shown, the graphical elements 252, 254, 256, 258 representing settings depict a bag reservoir or a peristaltic pump, and the graphical elements 261, 262, 264, 266, 268 representing alarms depict alarm bells. In other embodiments, graphical elements may depict any other apparatus that may be used in connection with an extracorporeal blood treatment.

An extracorporeal blood treatment may occur over multiple hours and/or days, or continuously, and the extracorporeal blood treatment system may log, or record, datasets over the entire treatment. The two-dimensional graph 230 may depict one or more datasets over a particular viewable time frame 280 of the extracorporeal blood treatment as shown in FIG. 7. The viewable time frame 280 may extend from a first end region 236 to a second end region 238 of the two-dimensional graph 230. In other words, the viewable time frame 280 may extend from the left side of the graph 230 to the right side of the graph 230.

The viewable time frame 280 may depict a time interval, or time period, selected by a user. As shown in FIG. 7, the time interval depicted in the viewable time frame 280 extends from 5:00 PM to 6:00 PM on 5 Jul. 2011. To adjust the time interval displayed in the viewable time frame 280, the historical data region 220 of the graphical user interface 210 may include a time interval selection region 270 as shown in FIG. 7. As shown in FIG. 7, the selected time interval is patient fluid removal, or PFR, as indicated by the acronym "PFR" located in the time interval selection region 270. The "PFR" time interval (e.g., which may be set based on time periods of removing fluid from the patient, hospital standards, etc.) may be a time interval extending between a selected period of time such as, e.g., 15 minutes, 30 minutes, 1 hour, 2 hours, etc., and as such, the time period displayed in the viewable time frame 280 is 1 hour.

Figure 11:
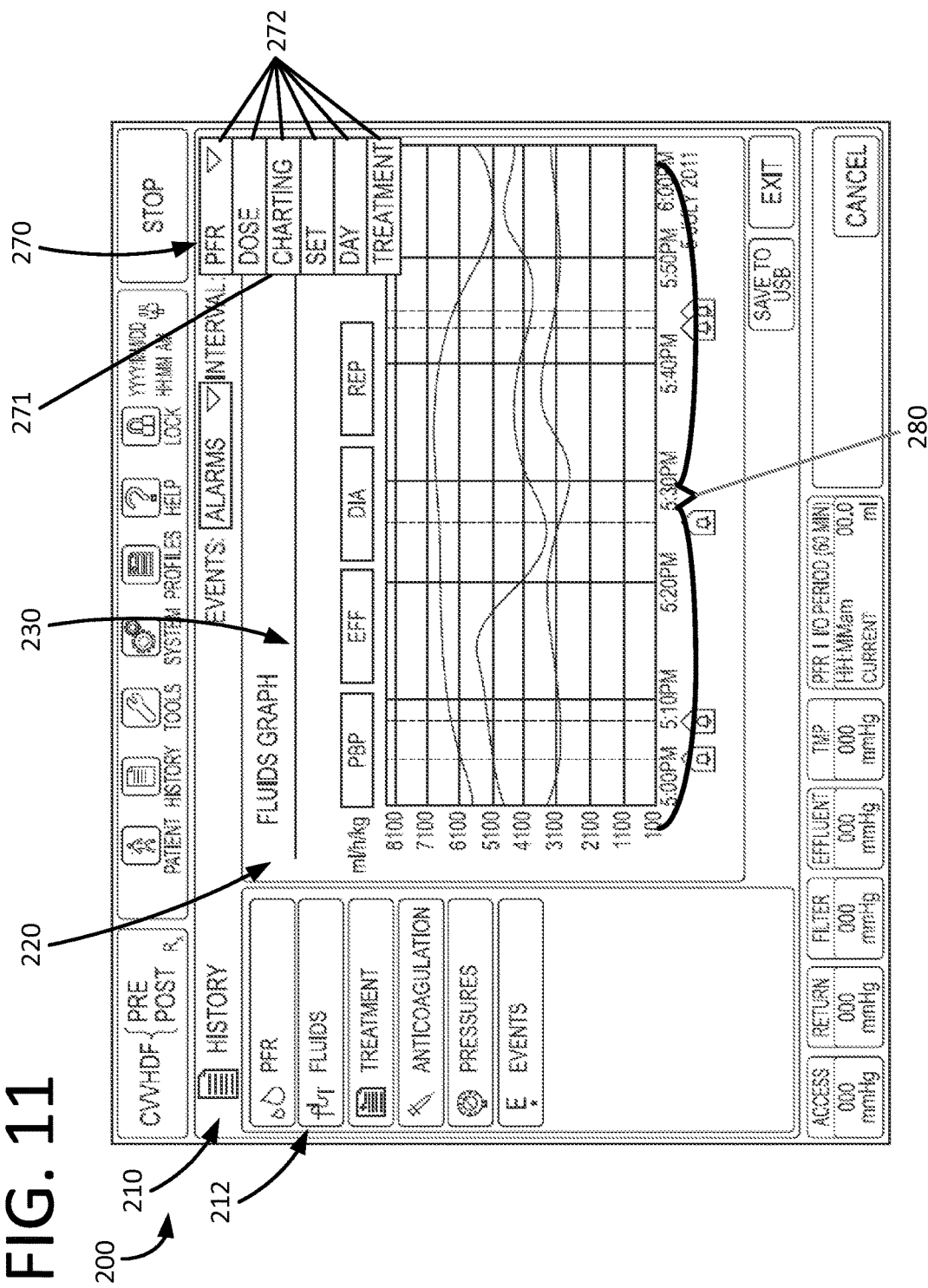

A user may select the time interval selection region 270 to change the time interval to another time interval as shown in FIG. 11. After selecting the time interval selection region 270, a time interval selection area 271 (e.g., menu, dialog, etc.) may appear, or be depicted, that includes each of a plurality of user selectable time intervals 272. As shown, the plurality of time intervals 272 may include "PFR," "Dose," "Charting," "Set," "Day," and "Treatment." The "Dose" time interval (e.g., which may be set by a user based on the treatment dose) may be a time interval extending between a selected period of time that is longer than the "PFR" time interval such as, e.g., 3 hours, 4 hours, 6 hours, 8 hours, etc. The "Charting" time interval (e.g., which may be set by a user based the length of the user's work shift, or any other time period) may be a time interval extending between a selected period of time that is also longer than the "PFR" time interval such as, e.g., 4 hours, 6 hours, 8 hours, etc. The "Set" time interval may be a time interval extending between each therapy set change (e.g., each filter and/or tubing set change, anticoagulation change, etc.). The "Day" time interval may be a time interval extending for an entire day. The "Treatment" time interval may be a time interval extending for an entire treatment (e.g., from start to finish of an extracorporeal blood treatment).

The plurality of time intervals 272 may include at least one dynamic time interval such as the "Set" time interval. As used herein, a dynamic time interval may be defined as a time interval that is determined as a function of an occurrence of at least one event associated with a treatment or the fluid treatment system. In other words, each dynamic time interval may be dependent on an occurrence of at least one event.

For example, an event, such as an alarm, may be the starting point or the ending pointing for a dynamic time interval. Further, for example, a first event, such as a first therapy set change, may be the starting point and a second event, such as a second therapy set change, may be the ending point for a dynamic time interval. Additionally, a point in time may be one of the starting point or ending point of a dynamic time interval as long as the other starting or ending point is based on an event. For example, an event, such as a nurse change, may be the starting point and a point in time, such as the present time, may be the ending point for a dynamic time interval. Further, for example, a point in time, such as 5:00 pm, may be the starting point and an event, such as a bag change, may be the ending point for a dynamic time interval. Such intervals may be added as selectable intervals in area 271.

Figure 12:
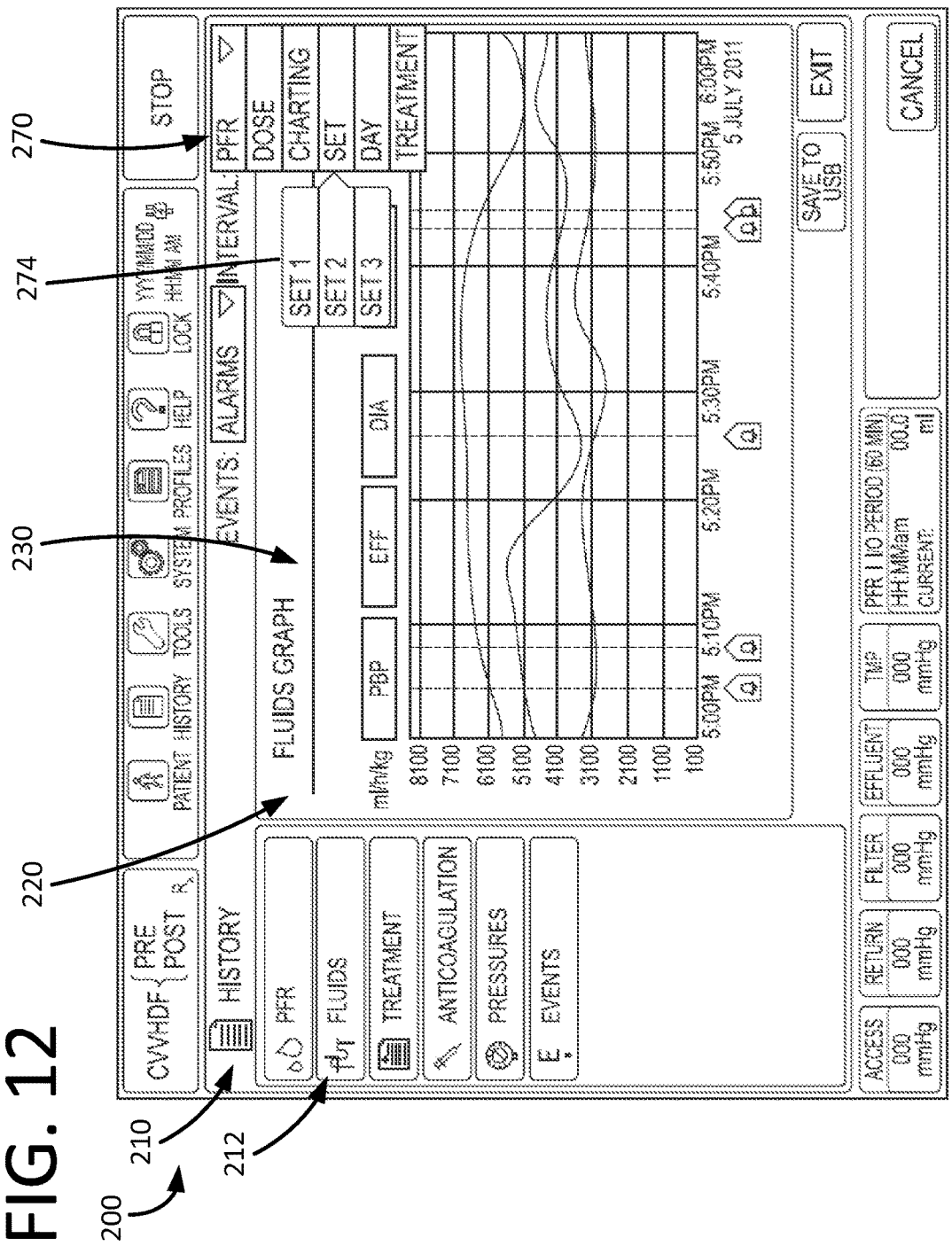

After a user has selected a time interval 272, the viewable time frame 280 may include the time interval selected. One or more selectable time intervals 272 may include additional options. For example, when a user selects the dynamic time interval "Set," an additional dynamic time interval area 274 (e.g., menu, dialog, etc.) may be depicted as shown in FIG. 12 to allow a user select which dynamic time interval defined by the therapy set changes should be depicted in the viewable time frame 280. As shown, the dynamic time interval area 274 may include "Set 1" that represents a time period from the installation of the first therapy set to the removal of the first therapy set, "Set 2" that represents the time period from the installation of the second therapy set (e.g., also the removal of the first therapy set) to the removal of the second therapy set, and "Set 3" that represents the time period from the installation of the third therapy set (e.g., also the removal of the second therapy set) to the removal of the third therapy set.

Figure 13:
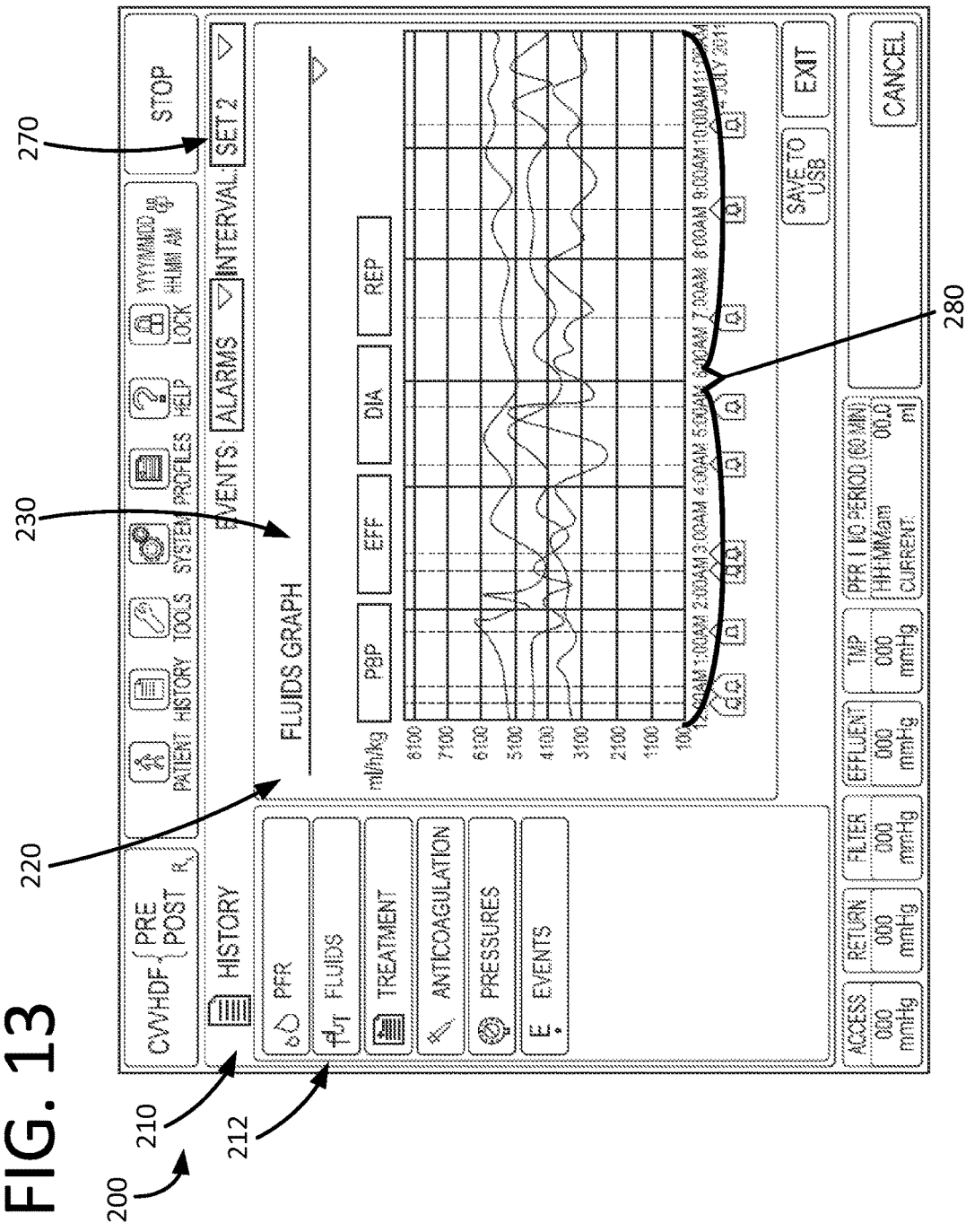

As shown in FIG. 13, a user has selected "Set 2" using the dynamic time interval area 274, and thus, the viewable time frame 280 has shifted to depict the time period from 12:00 AM to 11:00 AM, which is the time period extending from the installation of the second therapy set to the removal of the second therapy set.

Figure 14:
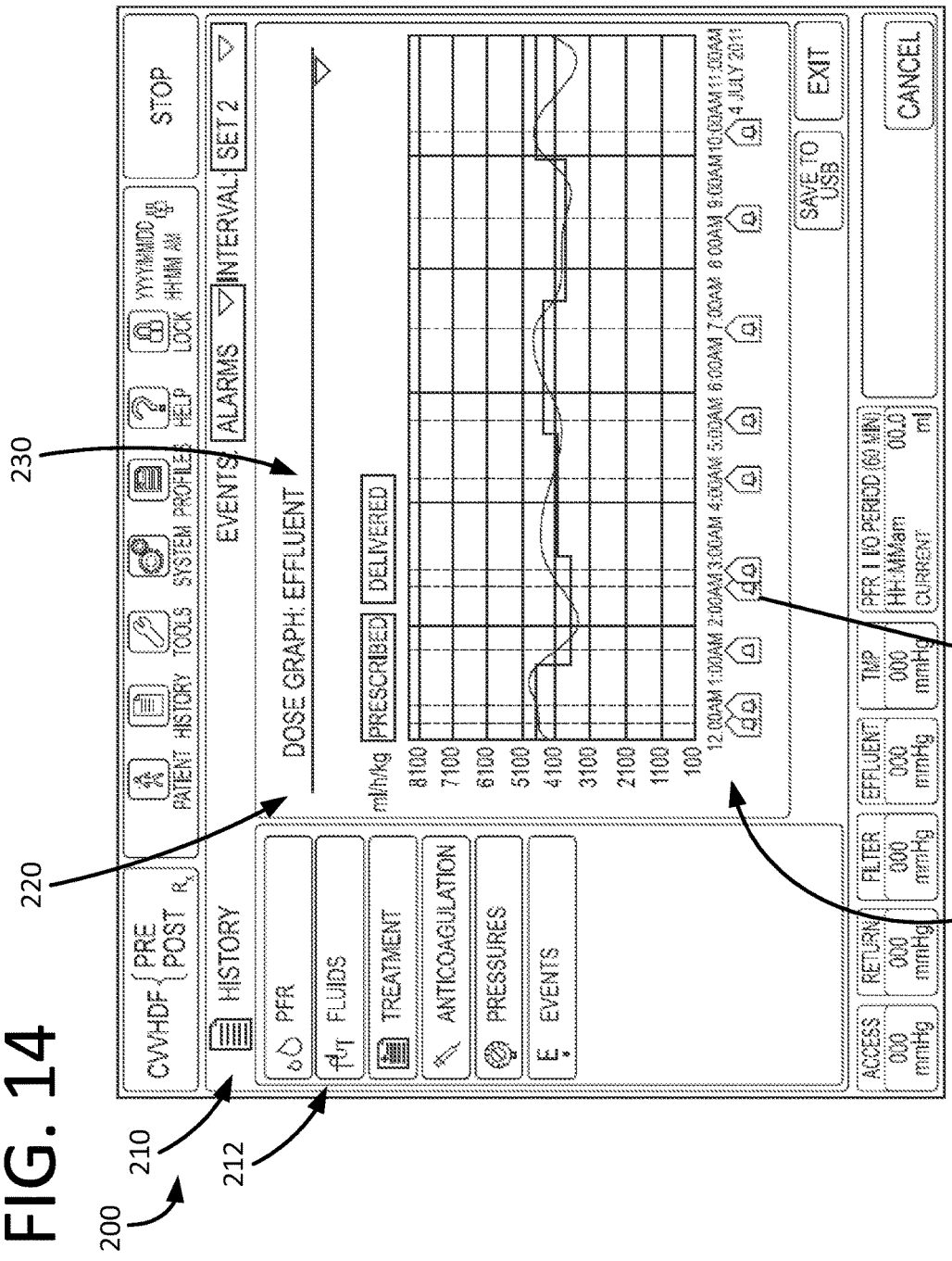

As described herein, a user may select a data type area 213 in the data type selection region 212 to change the historical data depicted in the historical data region 220. As shown in FIG. 14, a user has selected the "Treatment" data type of the plurality of data types 213 in the data type selection region 212, and thus, the data depicted in the historical data region 220 corresponds to treatment data (e.g., data related to the extracorporeal blood treatment). As shown, the treatment data includes a two-dimensional graph 230 depicting prescribed and/or delivered combinations of flow rates that may amount to a prescription. The two-dimensional graph 230 and remaining historical data region 220 may be similar to the two-dimensional graph 230 and historical data region 220 described herein with respect to the "Fluids" data type. For example, one or more datasets such as delivered effluent and delivered effluent may be selected using a dataset selection region to be depicted, or plotted, on the two-dimensional graph 230.

Further, an event display region 250 is depicted proximate (e.g., below) the two-dimensional graph 230 of the historical data region 220. A plurality of graphical elements, or icons, representing different events (e.g., alarms as shown) may be depicted in the event display region 250. Each of the graphical elements representing different events may be selected by a user seeking more information with respect to the particular selected event.

Figure 15:
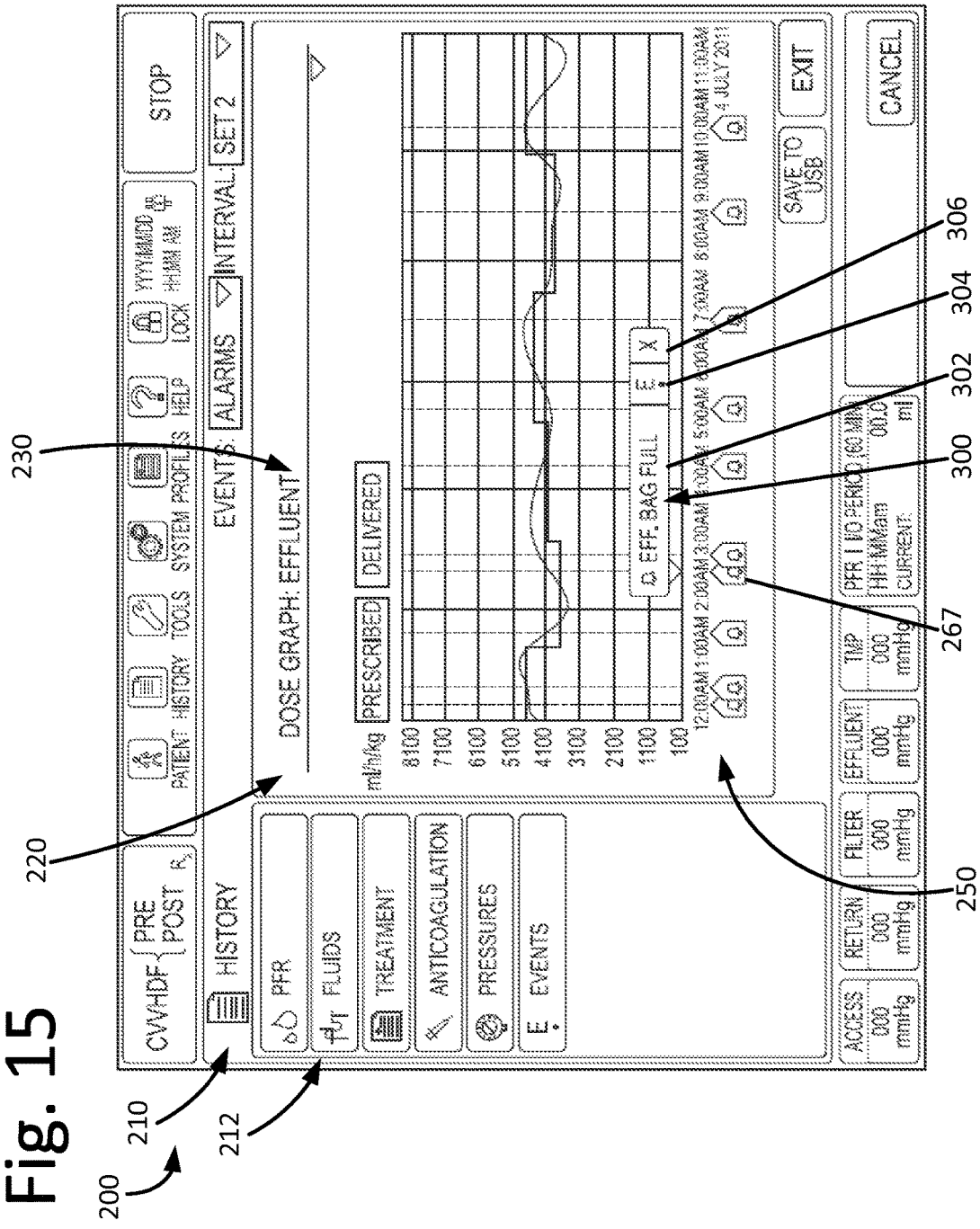

After a user has selected an event graphical element 267 representing an alarm, an event information area 300 (e.g., panel, pop-up, dialog, window, etc.) may be depicted in the historical data region 220 as shown in FIG. 15. In this embodiment, the event information area 300 is depicted over the two-dimensional graph 230 as a "pop-over" graphic. The event information area 300 may be configured to depict, or display, more information relevant to, or with respect to, the event represented by event graphical element 267.

As shown in the event information area 300, the event represented by the event graphical element 267 was an alarm that the effluent bag was full as indicated by the words "Eff. Bag Full" located in the alphanumeric area 302 of the event information area 300. The event information area further includes a list view icon, or area, 304 and a close icon, or area, 306. If a user desires to close (e.g., hide) the event informational panel (e.g., if the user has gathered enough information about the event, if the user desires to select another event, etc.), the user may select the close icon 306, which triggers the event information area 300 to disappear returning the graphical user interface 210 to the state shown in FIG. 14.

Figure 16:
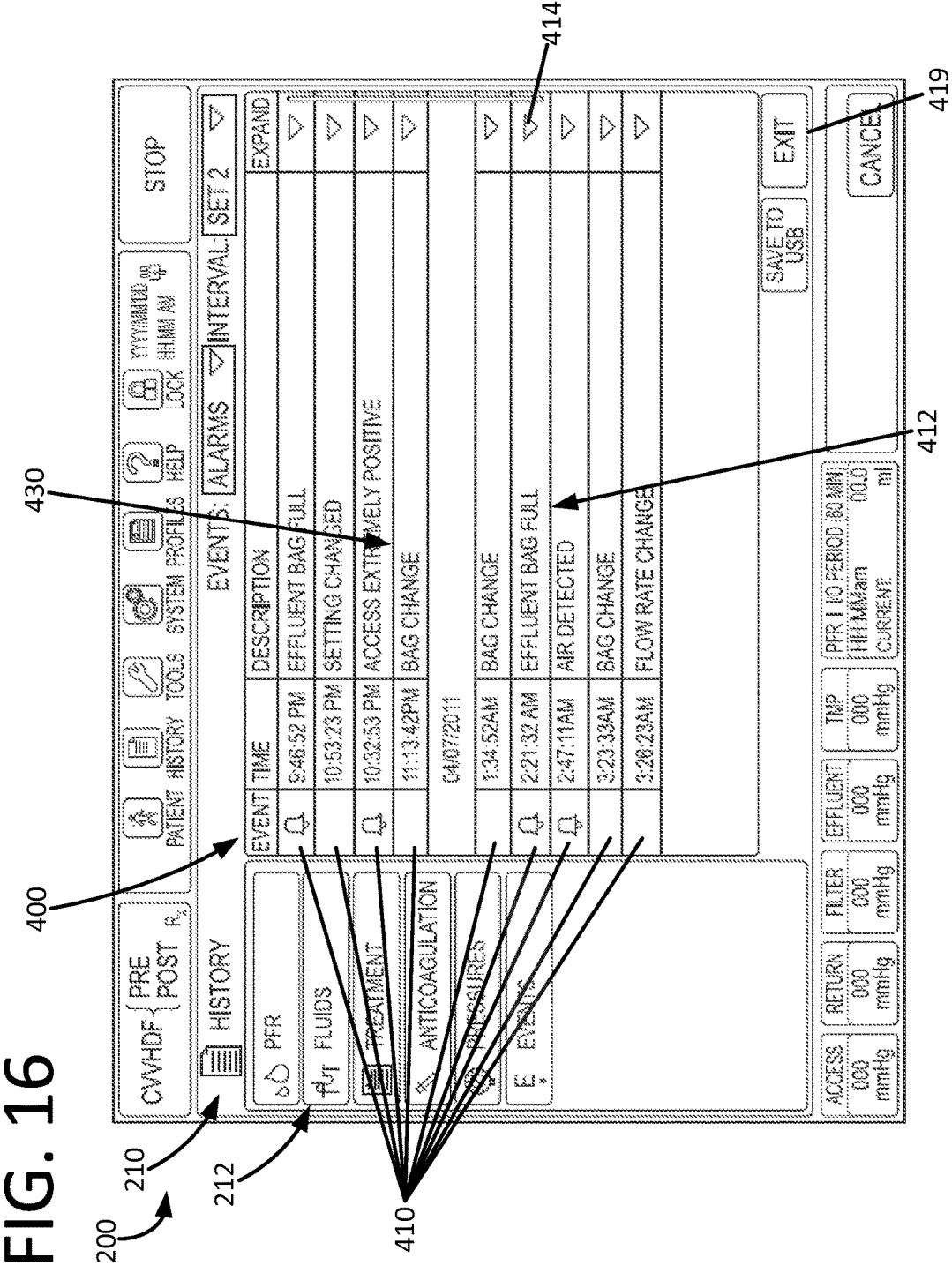
FIGS. 16-19 are screenshots of exemplary graphical user interfaces for displaying historical data chronologically on a list view for use in extracorporeal blood treatment systems, for example, such as shown generally in FIGS. 1-3.

A user may select the list view icon, or area, 304 to change the historical data region 220 to a list view of events 400 as depicted in FIG. 16. Also, a user may select the "Events" data type located in the data type selection region 212 to change the historical data region 220 to a list view of events 400 as depicted in FIG. 16. The list view 400 may include, or depict, a chronological list of events 410 with the selected event 412 (e.g., the event the user selected in FIG. 15) indicated by highlighting. The list of events 410 of the list view 400 may correspond to viewable time frame 280. For example, the list view 400 may display a chronological list of events 410 corresponding to at least a portion of the viewable time frame 280 of the two-dimensional graph 230. In at least one embodiment, only one of the two-dimensional graph 230 and the list view 400 may be displayed in the historical data region 220 on the graphical user interface 200 at the same time. In other words, the two-dimensional graph 230 and the list view 400 may not be displayed simultaneously in the historical data region 220. In at least one embodiment, the two-dimensional graph 230 and the list view 400 may be displayed in the historical data region 220 on the graphical user interface 200 at the same time. In other words, the two-dimensional graph 230 and the list view 400 may be displayed simultaneously in the historical data region 220.

In at least one embodiment, the list view 400 may only include the events 410 that have been selected using the event type selection region 260. Further, this feature may be enabled (e.g., to permit only the events in the list view 400 that have been selected using the event type selection region 260, to filter out the events that were not selected using the event type selection region 260, etc.) or disabled (e.g., permit or display all events in the list view 400 regardless of a selection using the event type selection region 260).

Figure 17:
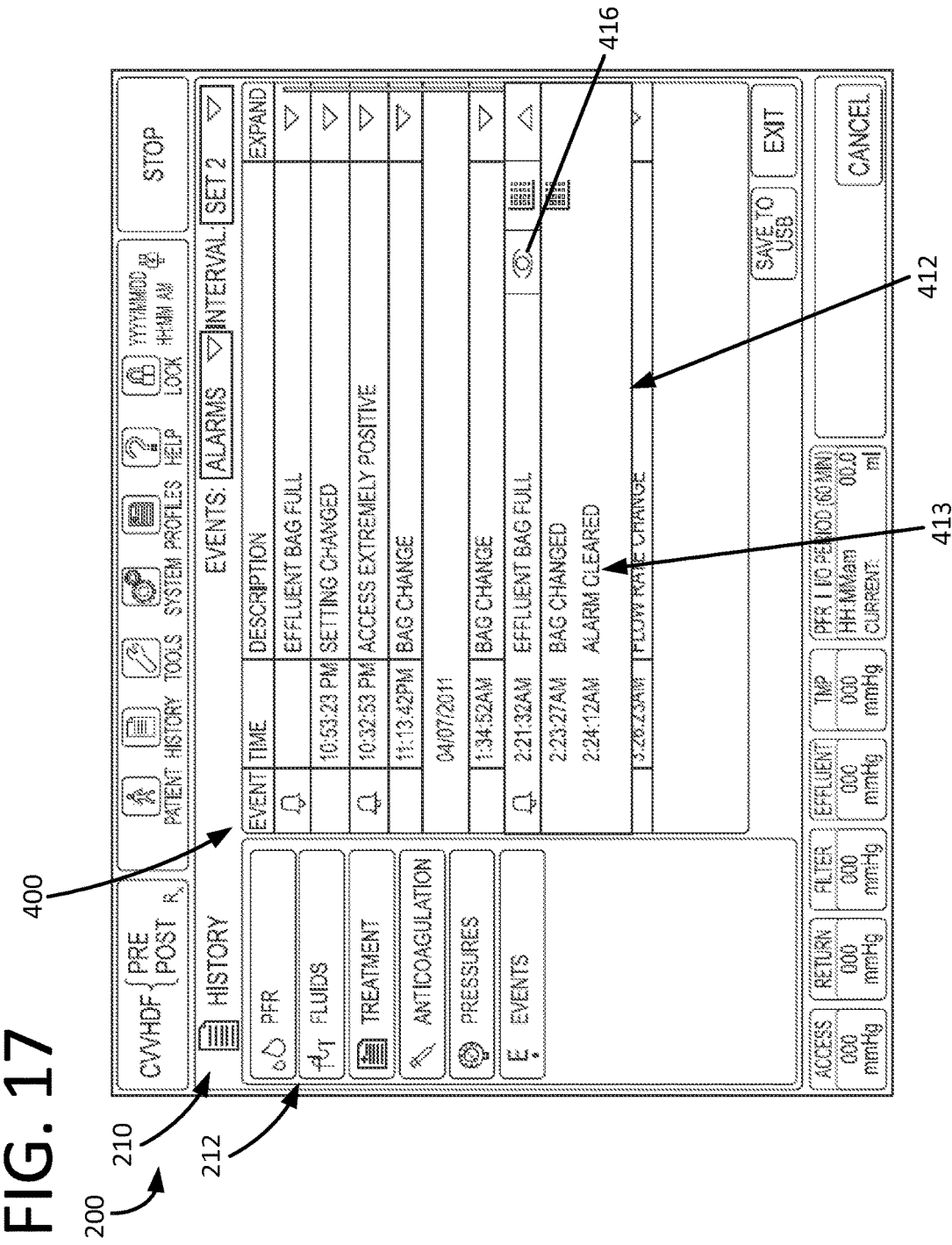

A user may select (e.g., by selecting the arrow icon 414 of FIG. 16) the selected event 412 to reveal, or display, additional information relevant to the selected event 412. As shown in FIG. 17, a user has selected the event 412 to depict more information (e.g., by selecting the arrow icon 414), and thus, an expanded information area 413 has been depicted. The expanded information area 413 includes additional information relevant to the selected event 412 such as, e.g., what triggered the event, how the event was cured or remedied, if the event was cleared from the system, flow rate information involved in the event, pressure information involved in the event, directions specified to the operator at the time of the event, etc.

Additionally, a user may decide to only view events of a particular type in the list view 400. For example, a user may decide that they want to see all access pressure alarms that have occurred during the course of the treatment. To do so, a user may select a "Show This Alarm Only" area, or button, located proximate the selected event, which may dismiss all events except for access pressure alarms. Similarly, only access pressure graphical elements may be displayed on all the graphs. In other words, an event type filter may be accessed from the list view 400.

Figure 18:
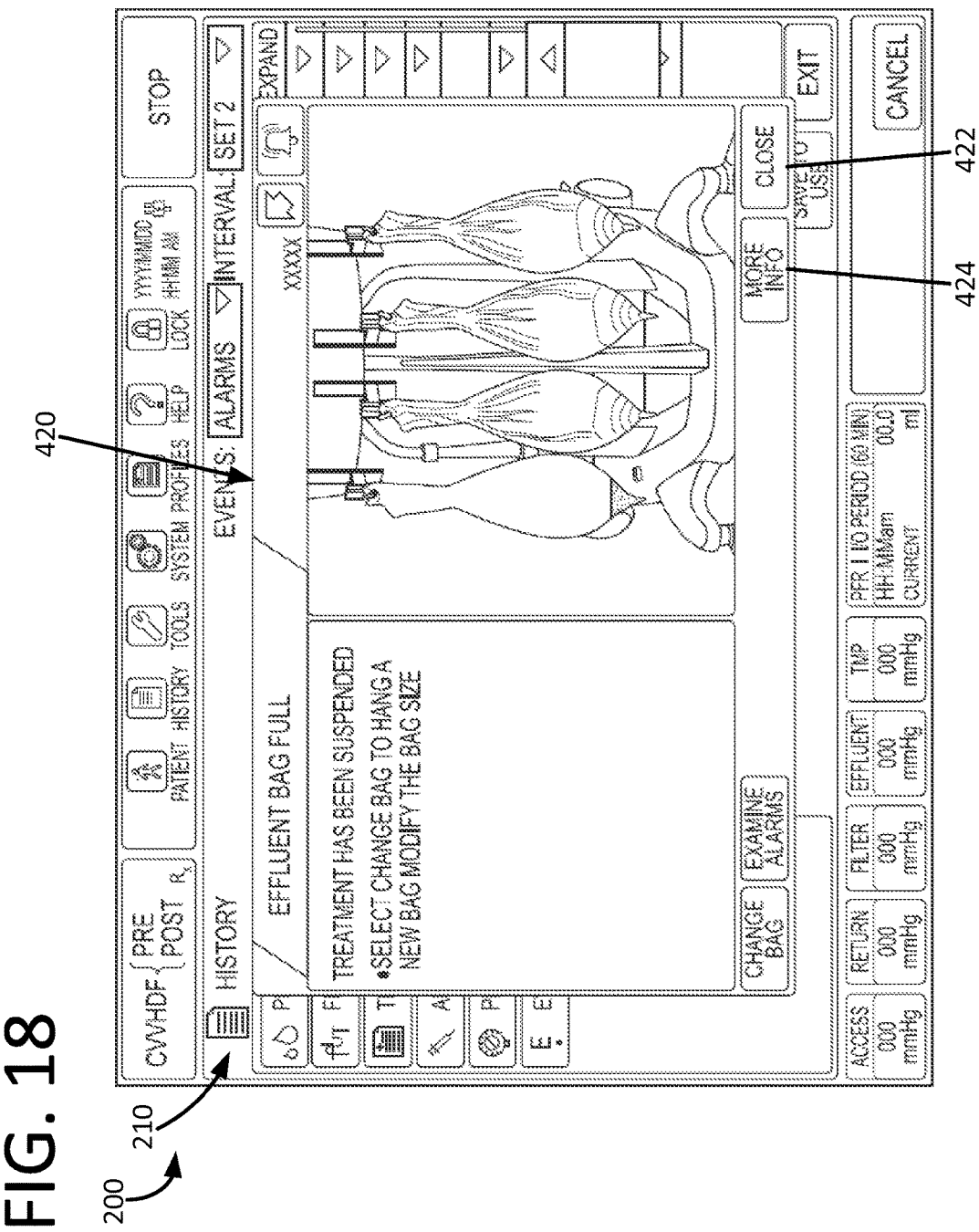

Additional information pertinent to the selected event 412 may be further displayed by selecting a more information graphical element, or icon, 416 of the expanded information area 413. The more information graphical element 416 may also be referred to as an event or alarm view (e.g., a view of an alarm screen that occurred during treatment). For example, event information region 420 as shown in FIG. 18 may be displayed after selecting the more information graphical element 416. The event information region 420 may be similar to the event information region displayed during treatment that corresponds to the selected event 412. To close, or remove from view, the event information region 420, a user may select the "Close" graphical element, or button, 422. To display even more information, or some more event information regions 420, a user may select the "More Information" graphical element, or button, 424 to provide more direction, or information, regarding the alarm or event depicted in the more event information region 420. Further, the buttons located on the lower left of the event information region 420 may be "greyed out" as not available since, e.g., the buttons represent selectable regions when the alarm is displayed during treatment.

When in the list view 400, a user may select another event to view additional information relevant to the selected event. For example, event 430 has been selected from the list view 400 depicted in FIG. 16, and the event 430 has been further selected to display the expanded information area 431 as shown in FIG. 19.

A user may return to the two-dimensional graph 230 from the list view 400 through various actions such as, e.g. selecting a graphical element, or area, in an expanded information area 413, 431, selecting a data type area of the data type selection region 212, selecting the "Exit" area/button 419, etc. When returning to the two-dimensional graph 230, the event selected in the list view 400 may be located within the viewable time frame 280. In other words, the viewable time frame 280 of the two-dimensional graph 230 may be described as shifting to a time period in which the selected event has occurred. Further, if the time interval has been set using the time interval selection region 270, the time interval displayed in the viewable time frame 280 may remain unchanged from when the historical data region 220 last displayed a two-dimensional graph 230. In other words, the scale of the viewable time frame 280 may not change despite the time period changing (e.g., the viewable time frame 280 may have shifted along the x-axis).

Figure 19:
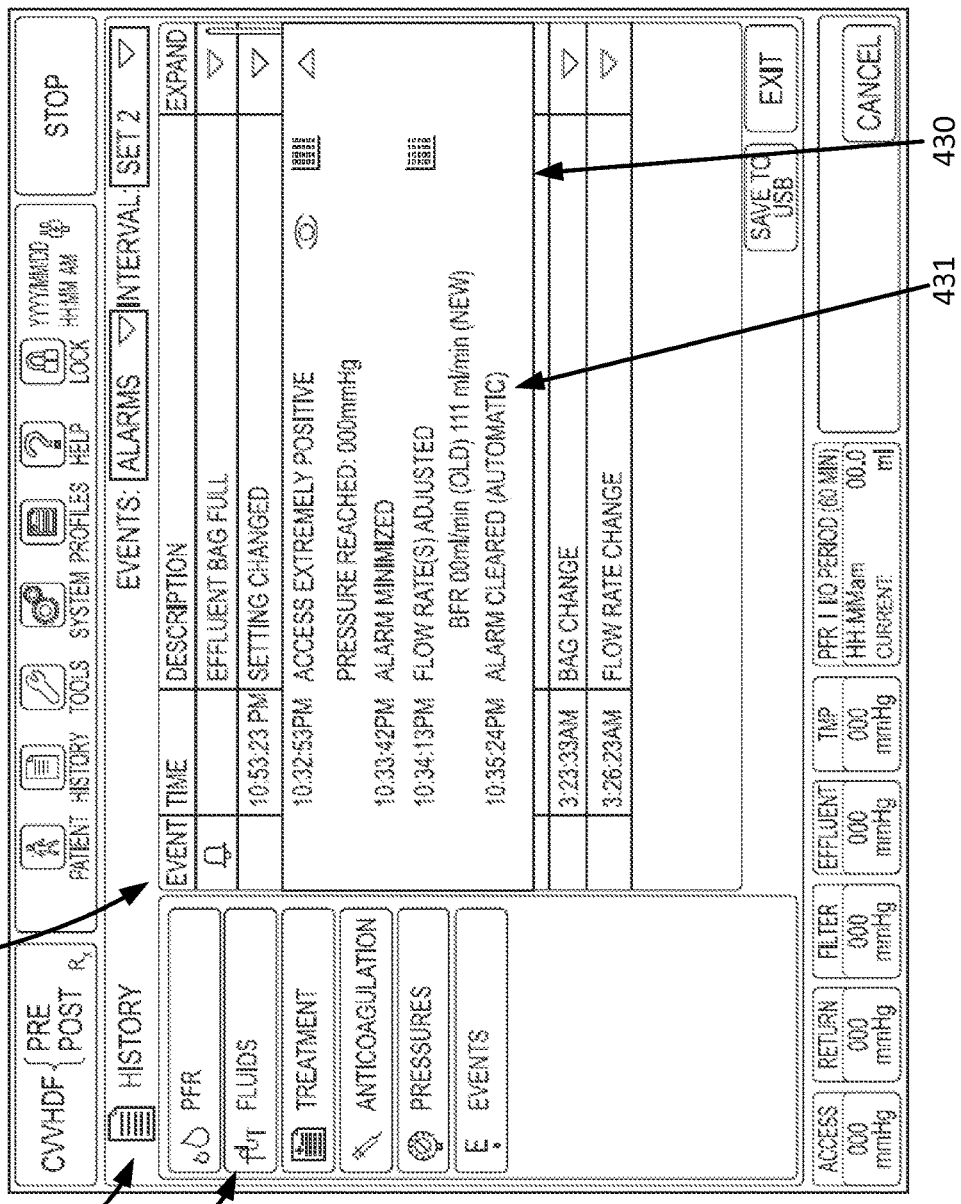
Figure 20:
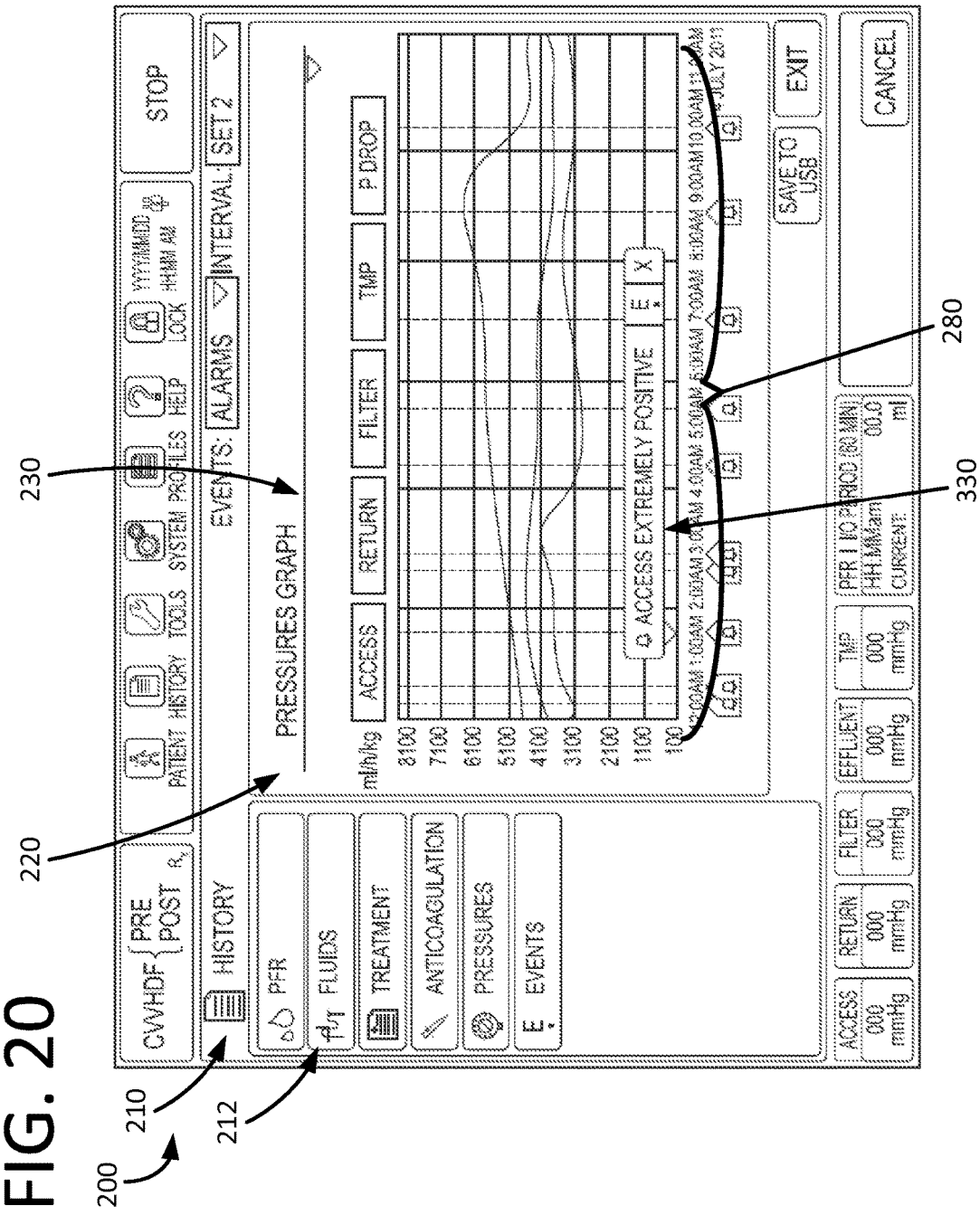

For example, a user has returned to the two-dimensional graph 230 in FIG. 20 after selecting the event 430 in FIG. 19. Further, as shown, the selected event 430, as indicated by displaying the event information area 330 related to the selected event 430, is located within the viewable time frame 280.

Figure 21:
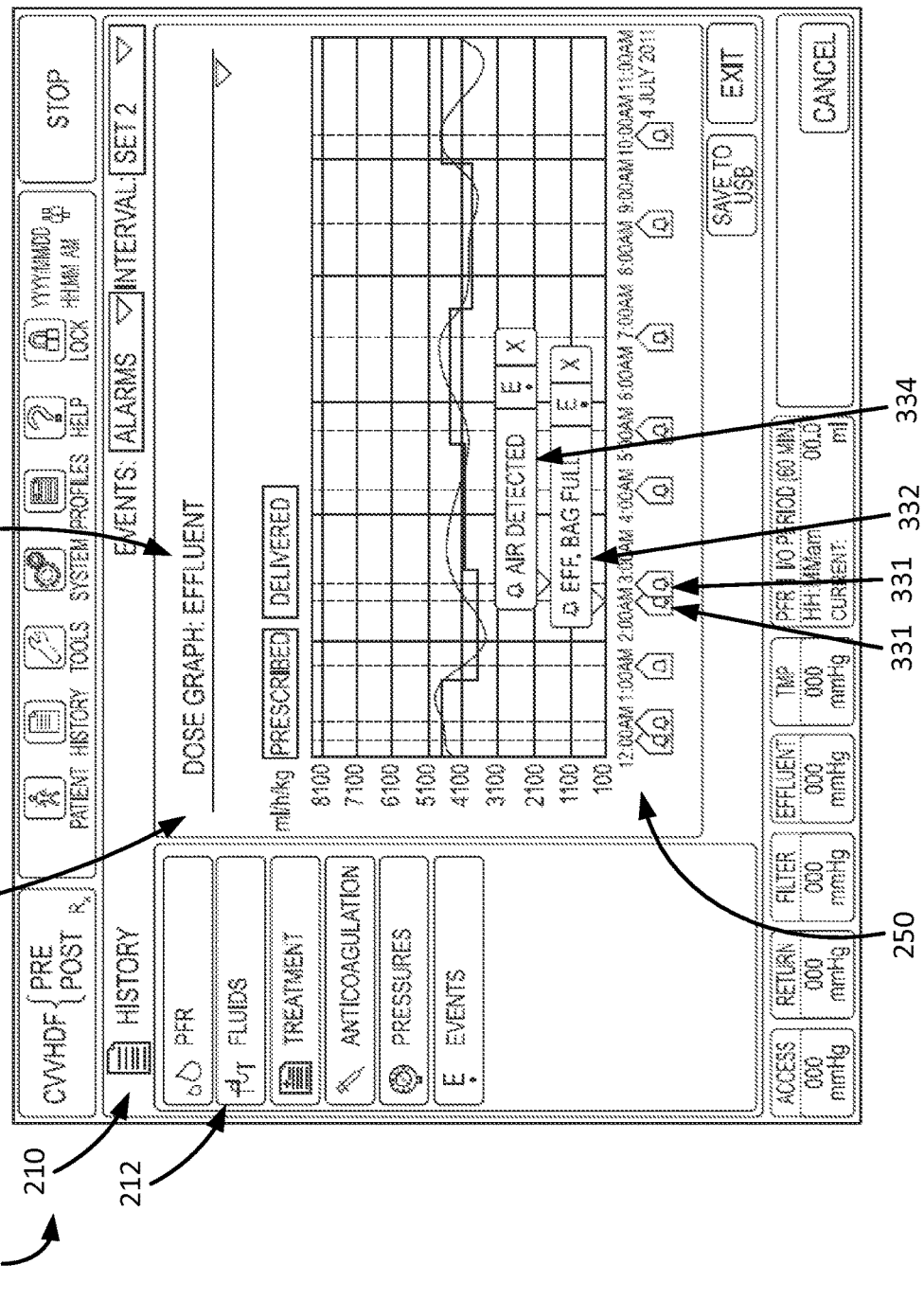

Two or more graphical elements representing events may be located in close proximity to one another in the event display region 250 as shown in FIG. 21. To select one of the two or more events located in close proximity to one another, a user may attempt to the select the desired event 331, and event information areas 332, 334 for both the desired event 331 and the event is close proximity thereto, respectively, may be displayed such that, e.g., a user may view the additional information relevant to the desired selected event and the event in close proximity thereto, a user may select to view additional information relevant to the desired selected event, etc. In other words, one or more event information areas may be displayed if one of the one or more graphical elements representing events is selected and the one or more graphical elements are in close proximity to one another (e.g., such that it may be challenging to select only one graphical element using a touchscreen).

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. An extracorporeal blood treatment system comprising:
 a display apparatus comprising a graphical user interface to assist a user in viewing historical data associated with one or more blood treatments, wherein the graphical user interface is configured to depict a two-dimensional graph and a time interval selection region, wherein the two-dimensional graph defines a time axis representing time and a value axis extending relative to the time axis and representing at least one value associated with a blood treatment or the blood treatment system used to carry out the blood treatment, wherein the two-dimensional graph defines a viewable time frame extending from a first end region to a second end region along the time axis, and wherein the graphical user interface is further configured to depict an event type selection region;
 an input interface configured to allow a user to select one or more of a plurality of historical datasets associated with the blood treatment or the blood treatment system used to carry out the blood treatment to be plotted on the two-dimensional graph; and
 a computing apparatus operatively coupled to the display apparatus and the input interface, wherein the computing apparatus is configured to:
  record data during a blood treatment, wherein the data comprises at least alarms occurring during the blood treatment and datasets associated with the blood treatment or the blood treatment system used to carry out the blood treatment,
  display on the graphical user interface the time interval selection region;
  allow a user to use the input interface to select a time interval of a plurality of different time intervals using the time interval selection region of the graphical user interface, wherein the plurality of different time intervals comprise at least one dynamic time interval, wherein the at least one dynamic time interval is a time interval that is determined as a function of an occurrence of at least one event associated with the treatment or the blood treatment system,
  display the one or more selected historical datasets associated with the blood treatment or the blood treatment system used to carry out the blood treatment plotted on the two-dimensional graph of the graphical user interface for the selected time interval in the viewable time frame,
  display an event type selection region on the graphical user interface;
  allow a user to use the input interface to select one or more event types of a plurality of different event types using the event type selection region of the graphical user interface, wherein the plurality of different event types comprises at least alarms occurring during a blood treatment; and
  display on the graphical user interface one or more graphical elements representing events of the one or more selected event types comprising at least alarms at locations proximate the two-dimensional graph when the events comprising at least alarms occurred during a blood treatment in the viewable time frame.

2. The system claim 1, wherein the at least one dynamic time interval extends from an event of the at least one event to the present time.

3. The system claim 1, wherein the at least one dynamic time interval extends from a first event of the at least one event to a second event of the at least one event.

4. The system claim 1, wherein the at least one event comprises one of filter set changes, logins, log accesses, screen locks, settings changes, bag changes, anticoagulation changes, advisories, flow rate changes, dose changes, and self-tests.

5. The system of claim 1, wherein the one or more graphical elements representing events are located below the time axis of the two-dimensional graph.

6. The system claim 1, wherein the one or more graphical elements representing events of each selected event type of the one or more selected event types comprise a different characteristic than the one or more graphical elements representing events of different selected event types of the one or more selected event types.

7. The system claim 1, wherein the computing apparatus is further configured to execute:
 allowing a user to use the input interface to select a specific event by selecting a graphical element of the one or more graphical elements representing events; and displaying an event information area comprising information relevant to the selected specific event in response to the selection of the graphical element.

8. The system claim 1, wherein the graphical user interface is further configured to depict a list view, wherein the list view comprises a chronological list of events, wherein the computing apparatus is further configured to execute:
   allowing a user to use the input interface to switch to a list view; and
   displaying the list view comprising a chronological list of events corresponding to at least a portion of the viewable time frame of the two-dimensional graph and including the event the user selected.

9. The system claim 7, wherein the computing apparatus is further configured to execute:
   displaying a list view icon in the event information area; and
   allowing a user to use the input interface to switch to a list view using the list view icon, wherein the list view displayed upon selection of the list view icon comprises a chronological list of events corresponding to at least a portion of the viewable time frame of the two-dimensional graph and including the event the user selected.

10. The system claim 8, wherein the computing apparatus is further configured to execute:
    allowing a user to use the input interface to scroll through the chronological list of events and select one or more specific events; and
    allowing a user to return to the two-dimensional graph, wherein the viewable time frame of the two-dimensional graph shifts to a time period in which the selected specific event occurred.

11. The system of claim 10, wherein the selected time interval remains unchanged.

12. The system claim 1, wherein the computing apparatus is further configured to execute:
    allowing a user to use the input interface to adjust the viewable time frame from the selected time interval; and
    displaying an indication on the graphical user interface proximate the two-dimensional graph indicating that the viewable time frame is different than the selected time interval.

13. The system of claim 12, wherein the indication on the graphical user interface proximate the two-dimensional graph indicating that the viewable time frame is different than the selected time interval comprises at least one change in a characteristic of the outline of the two-dimensional graph.

14. The system claim 1, wherein the graphical user interface is further configured to depict a dataset selection region, wherein the computing apparatus is further configured to execute:
    displaying on the graphical user interface a plurality of different dataset icons in a dataset selection region, wherein each dataset icon of the plurality of different dataset icons corresponds to a different dataset of a plurality of different datasets;
    allowing a user to use the input interface to select one or more datasets by selecting one or more dataset icons using the dataset selection region of the graphical user interface; and
    displaying on the two-dimensional graph the one or more selected datasets.

15. The system claim 1, wherein the graphical user interface is further configured to depict a data type selection region, wherein the computing apparatus is further configured to execute:
    displaying on the graphical user interface a plurality of different data type icons in a data type selection region, wherein each data type icon of the plurality of different data type icons corresponds to a different data type of a plurality of different data types;
    allowing a user to use the input interface to select one or more data types by selecting one or more data type icons using the data type selection region; and
    displaying on the two-dimensional graph one or more datasets of the one or more selected data types.

16. A method for an extracorporeal blood treatment system comprising:
    providing a graphical user interface to assist a user in viewing historical data associated with one or more blood treatments comprising a two-dimensional graph and a time interval selection region, wherein the two-dimensional graph defines a time axis representing time and a value axis extending relative to the time axis and representing at least one value associated with a blood treatment or the blood treatment system used to carry out the blood treatment, wherein the two-dimensional graph defines a viewable time frame extending from a first end region to a second end region along the time axis, and wherein the graphical user interface is further configured to depict an event type selection region;
    providing an input interface configured to allow a user to select one or more of a plurality of historical datasets associated with the blood treatment or the blood treatment system used to carry out the blood treatment to be plotted on the two-dimensional graph;
    recording data during a blood treatment, wherein the data comprises at least alarms occurring during the blood treatment and datasets associated with the blood treatment or the blood treatment system used to carry out the blood treatment;
    allowing a user to use the input interface to select a time interval of a plurality of different time intervals using the time interval selection region of the graphical user interface, wherein the plurality of different time intervals comprise at least one dynamic time interval, wherein the at least one dynamic time interval is a time interval that is determined as a function of an occurrence of at least one event associated with the treatment or the blood treatment system;
    displaying the one or more selected historical datasets associated with the blood treatment or the blood treatment system used to carry out the blood treatment plotted on the two-dimensional graph for the selected time interval in the viewable time frame;
    allowing a user to use the input interface to select one or more event types of a plurality of different event types using the event type selection region of the graphical user interface, wherein the plurality of different event types comprises at least alarms occurring during the blood treatment; and
    displaying on the graphical user interface one or more graphical elements representing events of the one or more selected event types comprising at least alarms at locations proximate the two-dimensional graph when the events comprising at least alarms occurred during the blood treatment in the viewable time frame.

17. An extracorporeal blood treatment system comprising:
a display apparatus comprising a graphical user interface to assist a user in viewing historical data associated with one or more blood treatments, wherein the graphical user interface is configured to depict a two-dimensional graph and an event type selection region, wherein the two-dimensional graph defines a time axis representing time and a value axis extending relative to the time axis and representing at least one value associated with a blood treatment or the blood treatment system used to carry out the blood treatment, wherein the two-dimensional graph defines a viewable time frame extending from a first end region to a second end region along the time axis;
an input interface configured to allow a user to select one or more of a plurality of historical datasets associated with the blood treatment or the blood treatment system used to carry out the blood treatment to be plotted on the two-dimensional graph; and
a computing apparatus operatively coupled to the display apparatus and the input interface, wherein the computing apparatus is configured to:
record data during a blood treatment, wherein the data comprises at least alarms occurring during the blood treatment and datasets associated with the blood treatment or the blood treatment system used to carry out the blood treatment,
display one or more selected historical datasets associated with the blood treatment or the blood treatment system used to carry out the blood treatment plotted on a two-dimensional graph of the graphical user interface in the viewable time frame;
display on the graphical user interface an event type selection region;
allow a user to use the input interface to select one or more event types of a plurality of different event types associated with the treatment or the blood treatment system using the event type selection region of the graphical user interface, wherein the plurality of different event types comprises at least alarms occurring during a blood treatment; and
display on the graphical user interface one or more graphical elements representing events of the one or more selected event types comprising at least alarms at locations proximate the two-dimensional graph when the events comprising at least alarms occurred during a blood treatment in the viewable time frame.

18. The system claim 17, wherein the one or more graphical elements representing events are located below the time axis of the two-dimensional graph.

19. The system claim 17, wherein the one or more graphical elements representing events of each selected event type of the one or more selected event types comprise a different characteristic than the one or more graphical elements representing events of different selected event types of the one or more selected event types.

20. The system claim 17, wherein the computing apparatus is further configured to execute:
allowing a user to use the input interface to select a specific event by selecting a graphical element of the one or more graphical elements representing events; and
displaying an event information area comprising information relevant to the selected specific event in response to the selection of the graphical element.

21. A method for an extracorporeal blood treatment system comprising:
providing a graphical user interface to assist a user in viewing historical data associated with one or more blood treatments comprising a two-dimensional graph and an event type selection region, wherein the two-dimensional graph defines a time axis representing time and a value axis extending relative to the time axis and representing at least one value associated with a blood treatment or the blood treatment system used to carry out the blood treatment, wherein the two-dimensional graph defines a viewable time frame extending from a first end region to a second end region along the time axis;
providing an input interface configured to allow a user to select one or more of a plurality of historical datasets associated with the blood treatment or the blood treatment system used to carry out the blood treatment to be plotted on the two-dimensional graph;
recording data during a blood treatment, wherein the data comprises at least alarms occurring during the blood treatment and datasets associated with the blood treatment or the blood treatment system used to carry out the blood treatment;
displaying the one or more selected historical datasets associated with the blood treatment or the blood treatment system used to carry out the blood treatment plotted on the two-dimensional graph of the graphical user interface in the viewable time frame;
allowing a user to use the input interface to select one or more event types of a plurality of different event types associated with the treatment or the blood treatment system using the event type selection region of the graphical user interface, wherein the plurality of different event types comprises at least alarms occurring during a blood treatment; and
displaying on the graphical user interface one or more graphical elements representing events of the one or more selected event types comprising at least alarms at locations proximate the two-dimensional graph when the events comprising at least alarms occurred during a blood treatment in the viewable time frame.

22. An extracorporeal blood treatment system comprising:
a display apparatus comprising a graphical user interface to assist a user in viewing historical data associated with one or more blood treatments, wherein the graphical user interface is configured to depict a two-dimensional graph and a list view, wherein the two-dimensional graph defines a time axis representing time and a value axis extending relative to the time axis and representing a value associated with a blood treatment or the blood treatment system used to carry out the blood treatment, wherein the two-dimensional graph defines a viewable time frame extending from a first end region to a second end region along the time axis, wherein the list view comprises a chronological list of events associated with the blood treatment or the blood treatment system used to carry out the blood treatment;
an input interface configured to allow a user to select one or more of a plurality of historical datasets associated with the blood treatment or the blood treatment system used to carry out the blood treatment to be plotted on the two-dimensional graph; and
a computing apparatus operatively coupled to the display apparatus and the input interface, wherein the computing apparatus is configured to:
record data during a blood treatment, wherein the data comprises at least alarms occurring during the blood treatment and datasets associated with the blood treatment or the blood treatment system used to carry out the blood treatment, display on a graphical user interface one or more selected historical datasets associated with the blood treatment or the blood treatment system used to carry out the blood treatment plotted on a two-dimensional graph in the viewable time frame, display on the graphical user interface one or more graphical elements representing events comprising at least alarms occurring during a blood treatment associated with the treatment or the blood treatment system at locations proximate the two-dimensional graph when the events comprising at least alarms occurred during the blood treatment in the viewable time frame, allow a user to use the input interface to switch to a list view from the two-dimensional graph, and display on the graphical user interface the list view comprising a chronological list of events corresponding to at least a portion of the viewable time frame of the two-dimensional graph, and wherein the computing apparatus is further configured to execute:

allowing a user to use the input interface to select a specific event comprising an alarm occurring during a blood treatment by selecting a graphical element of the one or more graphical elements representing events comprising the alarm occurring during a blood treatment proximate the two-dimensional graph;

displaying an event information area comprising information relevant to the selected specific event comprising the alarm occurring during a blood treatment and a list view icon; and allowing a user to use the input interface to switch to the list view by selecting the list view icon, wherein the list view displayed upon selection of the list view icon comprises a chronological list of events corresponding to at least a portion of the viewable time frame of the two-dimensional graph and including the event comprising the alarm selected by the user.

23. The system claim 22, wherein only one of the two-dimensional graph and the list view are displayed on the graphical user interface at the same time.

24. The system claim 22, wherein the computing apparatus is further configured to execute:

allowing a user to use the input interface to scroll through the chronological list of events when in list view and select a specific event; and allowing a user to return to the two-dimensional graph from the list view, wherein the viewable time frame of the two-dimensional graph shifts to a time period in which the selected specific event occurred.

25. A method for an extracorporeal blood treatment system comprising:

providing a graphical user interface to assist a user in viewing historical data associated with one or more blood treatments comprising a two-dimensional graph and a list view, wherein the two-dimensional graph defines a time axis representing time and a value axis extending relative to the time axis and representing a value associated with a blood treatment or the blood treatment system used to carry out the blood treatment, wherein the two-dimensional graph defines a viewable time frame extending from a first end region to a second end region along the time axis, wherein the list view comprises a chronological list of events associated with a blood treatment or the blood treatment system used to carry out the blood treatment;

providing an input interface configured to allow a user to select one or more of a plurality of historical datasets associated with the blood treatment or the blood treatment system used to carry out the blood treatment to be plotted on the two-dimensional graph;

recording data during a blood treatment, wherein the data comprises at least alarms occurring during the blood treatment and datasets associated with the blood treatment or the blood treatment system used to carry out the blood treatment;

displaying on a graphical user interface one or more selected historical datasets associated with the blood treatment or the blood treatment system used to carry out the blood treatment plotted on a two-dimensional graph in the viewable time frame;

displaying on the graphical user interface one or more graphical elements representing events comprising at least alarms associated with the blood treatment or the blood treatment system used to carry out the blood treatment at locations proximate the two-dimensional graph when the events comprising at least alarms occurred during a blood treatment in the viewable time frame;

allowing a user to use the input interface to switch to a list view from the two-dimensional graph; and displaying on the graphical user interface the list view comprising a chronological list of events corresponding to at least a portion of the viewable time frame of the two-dimensional graph, wherein the method further comprises:

allowing a user to use the input interface to select a specific event comprising an alarm occurring during a blood treatment by selecting a graphical element of the one or more graphical elements representing events proximate the two-dimensional graph;

displaying an event information area comprising information relevant to the selected specific event comprising the alarm occurring during a blood treatment and a list view icon; and allowing a user to use the input interface to switch to the list view by selecting the list view icon, wherein the list view displayed upon selection of the list view icon comprises a chronological list of events corresponding to at least a portion of the viewable time frame of the two-dimensional graph and including the event comprising the alarm selected by the user.

* * * * *